(12) United States Patent
Brazeau

(10) Patent No.: US 8,252,341 B2
(45) Date of Patent: Aug. 28, 2012

(54) ISOLATION OF GROWTH AND DIFFERENTIATING FACTORS FROM COLOSTRUM

(76) Inventor: Paul Brazeau, Sherbrooke (CA)

( * ) Notice: Subject to any disclaimer, the term of this patent is extended or adjusted under 35 U.S.C. 154(b) by 746 days.

(21) Appl. No.: 11/575,297

(22) PCT Filed: Sep. 14, 2005

(86) PCT No.: PCT/CA2005/001398
§ 371 (c)(1),
(2), (4) Date: Nov. 11, 2008

(87) PCT Pub. No.: WO2006/029518
PCT Pub. Date: Mar. 23, 2006

(65) Prior Publication Data
US 2009/0081181 A1    Mar. 26, 2009

Related U.S. Application Data

(60) Provisional application No. 60/614,556, filed on Oct. 1, 2004.

(30) Foreign Application Priority Data

Sep. 14, 2004    (WO) ................ PCT/CA2004/001676

(51) Int. Cl.
*A61K 35/20*    (2006.01)
(52) U.S. Cl. ....................................................... 424/535
(58) Field of Classification Search .................. None
See application file for complete search history.

(56) References Cited

U.S. PATENT DOCUMENTS

| 4,440,860 | A | * | 4/1984 | Klagsbrun .................... 435/384 |
| 4,582,580 | A | * | 4/1986 | Goudal et al. ................ 210/656 |
| 4,644,056 | A | * | 2/1987 | Kothe et al. ................. 424/157.1 |
| 4,816,563 | A | * | 3/1989 | Wilson et al. ................. 530/344 |
| 4,866,037 | A | * | 9/1989 | Delespesse ................ 424/278.1 |
| 5,147,548 | A | * | 9/1992 | Hies et al. ..................... 210/639 |
| 5,500,229 | A | | 3/1996 | Aalto |
| 6,277,813 | B1 | | 8/2001 | Kelly |
| 6,875,459 | B2 | | 4/2005 | Kopf |
| 2005/0092684 | A1 | * | 5/2005 | Keech et al. ................. 210/645 |
| 2007/0161780 | A1 | * | 7/2007 | Georgiades et al. .......... 530/350 |
| 2007/0212367 | A1 | * | 9/2007 | Keech ......................... 424/185.1 |
| 2009/0028990 | A1 | * | 1/2009 | Kwon et al. ...................... 426/2 |

FOREIGN PATENT DOCUMENTS

| CN | 1557340 | 12/2004 |
| CN | 1557837 | 12/2004 |
| EP | 0173999 | 3/1986 |
| EP | 0918464 | 4/2001 |
| EP | 0711171 | 4/2002 |
| WO | WO9308264 | 4/1993 |
| WO | WO9500155 | 1/1995 |
| WO | WO9743905 | 11/1997 |
| WO | WO9811904 | 3/1998 |
| WO | WO9811910 | 3/1998 |
| WO | WO9956758 | 11/1999 |

OTHER PUBLICATIONS

Pakkanen, R. et al., "Bovine colostrum fraction as a serum substitute . . . ", Appl. Microbiol. Biotechnol., 1992, pp. 451-456, vol. 37-4.
http://www.nhlbi.nih.gov/meetings/workshops/brush-cell.htm.
http//www.sbs.utexas.edu/shankland/lc11dig1.htm.
Extended European Search Report mailed May 10, 2011, in Application No. 05784909.3.
Anonymous: "Colostrum", Wikipedia, the free encyclopedia; retrieved from the internet: URL:http//en.wikipedia.org/wiki/Colostrum; Mar. 14, 2011.
Uruakpa F O et al.; Colostrum and its benefits; A review:, Nutrition Research, vol. 22, No. 6, Jun. 2002, pp. 755-767.
Playford Raymond J et al.: Colostrum and milk-derived peptide growth factors for the treatment of gastrointestinal disorders:, American Journal of Clinical Nutrition, vol. 72, No. 1, Jul. 2000, pp. 5-14.

* cited by examiner

*Primary Examiner* — Christopher R. Tate

(57) ABSTRACT

The present invention concerns a novel process for isolating growth and differentiating factors present in colostrum, all in a natural way. This process is characterized by maturation steps (controlled mild acid hydrolysis) and physical steps (molecular filtration) which optimize recovery of measured growth factors and their ability to entice a response on human cells. Advantageously, this process allows the derivation and isolation of growth and differentiating factors with highly disparate sizes (or molecule weights) in pools. These pools can be used in select and varied ways, including cosmetic, cosmeceutical, nutraceutical, dermatological, pharmaceutical, medical and veterinary applications. It can also be used as a replacement to fetal calf serum to promote cell proliferation, and above all, cell differentiation.

4 Claims, 24 Drawing Sheets

FIGURE 2
GROWTH FACTORS FOUND IN COLOSTRUM FRACTIONS

COLOSTROSERUM

*** HIGHEST CONCENTRATION
** SECOND HIGHEST CONCENTRATION
* THIRD HIGHEST CONCENTRATION

FILTER 0.2 um

LP1 (0.2 um to 5 KDa) — all fractions go through this 0.2 um filter limit
13 GFs: IGF-1 *, IGFBP-3, TGF-B2, TGF-B1 *, TGF-A *, PDGF-AA ***, HGF, FGF-4 *, KGF (FGF-7), FGF-2 ***, BMP-2, SCF, TNF-B
≈ 90 g/kg

LP2 (300 KDa to 5 KDa)
15 GFs: IGF-1, IGFBP-3 *, TGF-B2 *, TGF-B1, TGF-A, PDGF-AA *, HGF, FGF-4, KGF (FGF-7) *, FGF-2 *, BMP-2, SCF *, TNF-B **
≈ 55 g/kg

LP3 (150 KDa to 5 KDa)
13 GFs: IGF-1, IGFBP-3, TGF-B2, TGF-B1, TGF-A, PDGF-AA **, HGF *, FGF-4, KGF (FGF-7), FGF-2, BMP-2, SCF, TNF-B
≈ 35 g/kg

LP4 (50 KDa to 5 KDa)
13 GFs: IGF-1, IGFBP-3, TGF-B2, TGF-B1, TGF-A, PDGF-AA, HGF, FGF-4, KGF (FGF-7), FGF-2, BMP-2, SCF, TNF-B
≈ 25 g/kg

LP1-LP3 (0.2 um to 150 KDa)
IGF-1, IGFBP-3 , TGF-B2 , TGF-B1 *, TGF-A , PDGF-AA, HGF , FGF-4 , KGF (FGF-7) *, FGF-2 , BMP-2 , SCF, TNF-B *
≈ 50 g/kg

LP3-LP5 (150 KDa to 15 KDa)
12 GFs: IGF-1, IGFBP-3, TGF-B2, TGF-B1, TGF-A, HGF, FGF-4, KGF (FGF-7), FGF-2, BMP-2 *, SCF, TNF-B
≈ 30 g/kg

LP5 (15 KDa to 5 KDa)
10 GFs: IGF-1, IGFBP-3, HGF, TGF-A, FGF-4, FGF-2, KGF (FGF-7), BMP-2, SCF
≈ 20 g/kg

LP1-LP5 (0.2 um to 15 KDa)
13 GFs: IGF-1 *, IGFBP-3 *, TGF-B2 *, TGF-B1 *, TGF-A , PDGF-AA *, HGF , FGF-4 *, KGF (FGF-7) , FGF-2 *, BMP-2 *, SCF *, TNF-B ***
≈ 70 g/kg

Filter sizes: 300 KDa, 150 KDa, 50 KDa, 15 KDa, 3 KDa

FIGURE 3
Summary of ELISA test results
GFs / kg extracted (ng / kg)

| | Product Temp. | amount extracted g/kg | IGF-1 ng/kg | IGFBP-3 ng/kg | TGF-B2 ng/kg | TGF-B1 ng/kg | TGF-A ng/kg | PDGF-AA ng/kg | HGF ng/kg | FGF-4 ng/kg | KGF (FGF-7) ng/kg | FGF-2 ng/kg | BMP-2 ng/kg | SCF ng/kg | TNF-B ng/kg |
|---|---|---|---|---|---|---|---|---|---|---|---|---|---|---|---|
| LP1 208 | 22 | 90 | 89,962.20 | 144.08 | 1,730.59 | 699.60 | 155.38 | 313.58 | 16.28 | 72.00 | 7.20 | 10.29 | 21.69 | 16.29 | 13.69 |
| LP2 202 | 20/22 | 55 | 31,823.35 | 157.85 | 3,662.89 | 574.20 | 42.70 | 174.98 | 12.69 | 36.80 | 7.70 | 9.90 | 17.69 | 17.69 | 14.85 |
| LP3 201 | 22 | 35 | 9,618.90 | 45.20 | 872.08 | 129.35 | 29.70 | 169.38 | 18.35 | 31.85 | 1.75 | 4.90 | 15.75 | 7.35 | 8.30 |
| LP3 220 | 34/36 | 35 | 38,487.50 | 68.98 | 1,394.60 | 218.75 | 47.89 | 86.45 | 24.83 | 14.00 | 9.60 | 5.95 | 22.85 | 9.10 | 12.69 |
| LP4 206 | 20/22 | 28 | 4,799.75 | 22.45 | 82.58 | 2.25 | 15.75 | 6.35 | 24.75 | 6.08 | NS | 1.79 | 9.20 | 8.25 | 1.75 |
| LP4 223 | 32/34 | 25 | 6,157.50 | 17.03 | 107.50 | 2.30 | 13.80 | 2.00 | 2.15 | NS | 6.29 | 2.00 | NS | 1.29 | 2.15 |
| LP5 229 | 33/36 | 20 | 5,930.80 | 13.80 | NS | NS | 7.05 | NS | 6.80 | 22.50 | 1.00 | 0.60 | 94.80 | 4.03 | 0.60 |
| LP1-LP2 225 | 23 | 15 | 13,411.25 | 40.28 | 759.08 | 99.60 | 12.85 | NS | 13.20 | 22.90 | 5.90 | 1.65 | 15.04 | 5.93 | 6.03 |
| LP1-LP3 227 | 24 | 50 | 142,488.90 | 186.29 | 11,387.58 | 993.59 | 119.58 | 124.90 | 79.90 | 84.30 | 16.00 | 7.90 | 51.90 | 22.99 | 14.08 |
| LP4-LP5 213 | 21/25 | 40 | 72,154.18 | 24.52 | 876.36 | 63.99 | 93.28 | 17.29 | 6.03 | 14.97 | 1.21 | 3.22 | 8.86 | 4.21 | 6.03 |
| LP3-LP5 228 | 36/38 | 30 | 28,265.70 | 9.00 | 102.60 | 58.70 | 55.80 | NS | 13.50 | 38.80 | 1.88 | 2.40 | 23.10 | 3.08 | 1.50 |
| LP1-LP5 231 | 33/36 | 70 | 220,134.03 | 354.98 | 17,662.30 | 5,411.90 | 333.08 | 112.80 | 79.96 | 129.50 | 15.40 | 12.60 | 89.98 | 24.50 | 29.38 |

NS = not significant

21 Human Growth Factors were tested.

The 13 Growth Factors listed above were in sufficient amount to be active on human primary cells.

Trace amounts, insufficient to have an effect on cells, were found of the following Growth Factors:
VEGF
TNF-A
BMP-4
PDGF-AB The following Growth Factors found absent from tested fractions:
PDGF-BB
EGF
PlGF
IGFBP-1

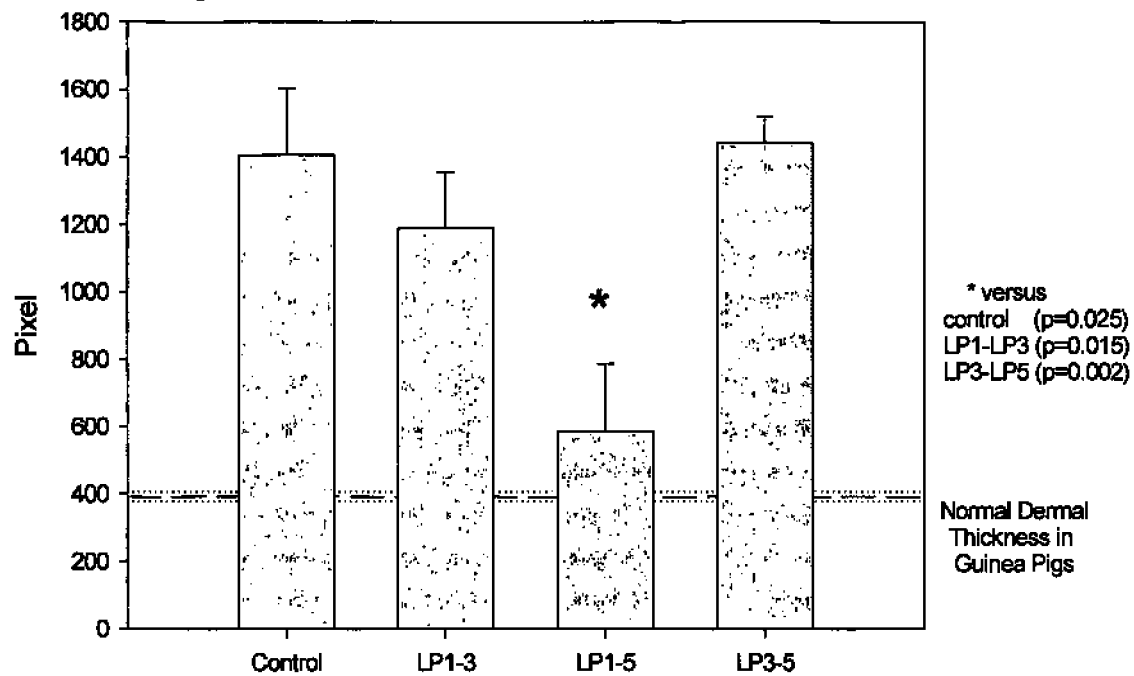
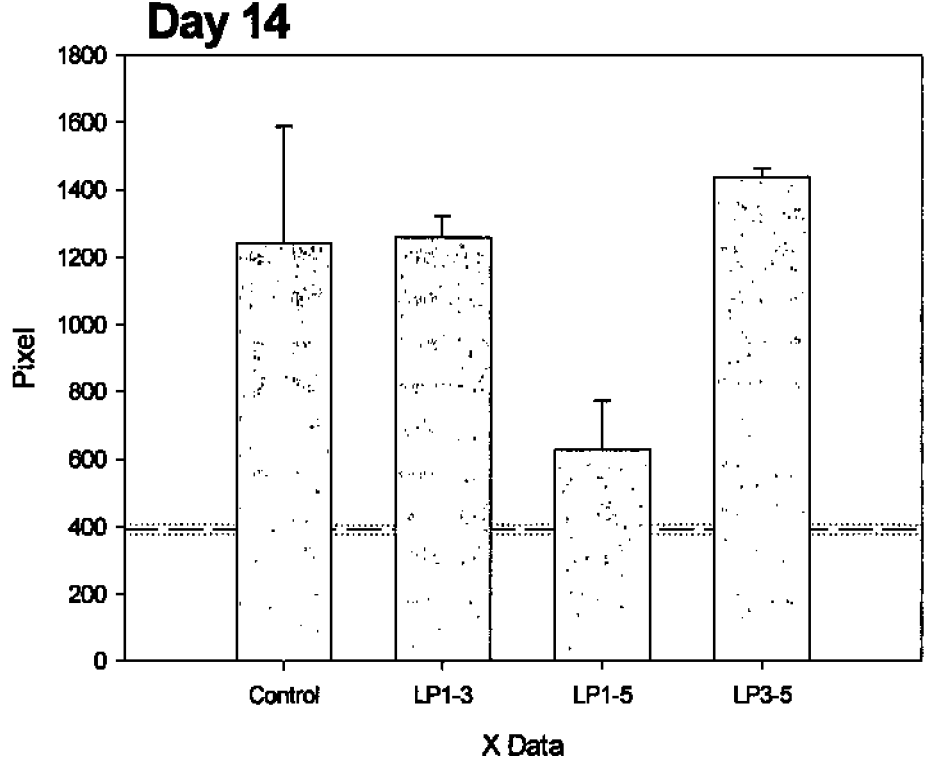
FIGURE 18

ISOLATION OF GROWTH AND DIFFERENTIATING FACTORS FROM COLOSTRUM

CROSS REFERENCE TO RELATED APPLICATION

This application represents the U.S. National Stage Filing under 35 U.S.C. §371 of International Application No. PCT/CA2005/001398, filed Sep. 14, 2005, which was published in English, designated/elected the United States of America, and claims priority to International Application No. PCT/CA2004/001676 filed on Sep. 14, 2004 and to U.S. Provisional Patent Application No. 60/614,556, filed Oct. 1, 2004, all of which are incorporated by reference into the present application in their entirety for all purposes.

FIELD OF THE INVENTION

The present invention relates to a novel process for isolating growth and differentiating factors from colostrum. This process is characterized by maturation steps (controlled mild acid hydrolysis) and physical steps (molecular filtration). The invention further includes the use of the growth and differentiating factors derived from this process in prophylactic, therapeutic, cosmetic, cosmeceutical, dermatological, pharmaceutical, medical, veterinary or surgical (burn wounds, wounds, etc.) applications.

BACKGROUND OF THE INVENTION

Colostrum is a thick, yellow fluid produced by mammary glands during the first few days after birth. It provides life-supporting immune (gamma globulin) and growth factors that ensure the health and vitality of a newborn.

The identities and functions of many of the bioactive principles of colostrum milk remain to be elucidated. However, colostrum is known to be a source of numerous bioactive hormones and growth factors, many of which have been demonstrated to influence intestinal growth, cell differentiation, and the development of the immune and enteroendocrine systems when administered in isolation.

Growth factors may be defined as proteins of 5 to 680 kDa that possess growth modulating bioactivities. Their biological actions also include the modulation and facilitation of the expression of cellular phenotype. To exert biological effects, growth factors must interact with specific high-affinity membrane receptors that activate appropriate signal transduction/second messenger cascades.

In their natural state, most growth factors are inert on human cells and have very high molecular weights (340-580 kDa). In order to become active, these growth factors need to be released from their inactive original forms either through hydrolysis or temperature change, or both.

Interestingly, even growth factors from non-human origin, such as those derived from porcine or bovine colostrum, when converted into their active forms, have been found to be active on human cells. This can be explained by the fact that the active forms of smaller molecular weight are almost completely homologous to the corresponding human growth factors. This has been found to be the case, for example, for the following families of factors: IGFs (1-3), TFGs β (1-3), PDGFs (AA, AB, BB), BMPs (1-24) and FGFs (1-16). These factors, when in active form, are recognized for their ability to proliferate and/or differentiate the stem cells of a newborn.

U.S. Pat. No. 6,277,813 (Kelly) describes the extraction of a novel growth factor from porcine colostrum. The process for extracting this growth factor, identified as CDGF for "Colostrum Derived Growth Factor", includes the following steps: (1) separating all components of colostrum having a molecular weight below 200 kDa and discarding all components having a lower molecular weight; (2) treating the product of step 1 with dithiothreitol and boiling for 10 minutes; and (3) centrifuging the mixture of step (2) to spin down any precipitated matter and recovering the CDGF located in the supernatant.

U.S. Pat. No. 5,500,229 (Aalto et al.) discloses a colostral fraction having a low endotoxin, protein and immunoglobulin concentration. The colostral fraction is obtained through ultrafiltration of defatted colostrum using a membrane having a molecular weight cut off of 100 kDa and is intended for use as a supplement in cell culture media. The colostral fraction is said to be extremely useful either alone or when complemented by other supplements for replacing partially or completely fetal bovine serum in widely used cell culture media. The patent describes the effectiveness of the colostral fraction in the cultivation of hybridoma cells. (This invention is also described in Appl Microbiol Biotechnol (1992) 37: 451-456.)

European Patent No. 918464 (Adler et al.) discloses a process for preparing a colostral milk product from which casein has been largely removed and the colostrum has been defatted. The defatted and largely decaseinated colostrum is passed through an ultrafiltration column with an exclusion molecular mass of approximately $10^6$. The product obtained can be further filtered using columns with exclusion molecular masses of 300 kDa and/or 150 kDa and/or 50 kDa and/or 30 kDa and/or 20 kDa and/or 10 kDa and/or 5 kDa and/or 1 kDa and/or 0.5 kDa. The resulting products are said to be suitable for use as an additive for drugs, food supplements, beverages, baby food, animal food, beverages in intensive sport for muscle protection or for reducing the muscular recovery phase, and for the prevention and treatment of bacterial, viral and mycotic infections.

Chinese Patent No. 1557837 (Gao Chunping) describes a process to separate insulin-like growth factor, immunoglobulins and casein from bovine colostrum. Colostrum is defatted and acidified to separate the insulin-like growth factor from binding, and the insulin-like growth factor is isolated through ultrafiltration, concentrated and freeze dried to obtain a powder. Immunoglobulins are separated through ultrafiltration and concentrated to prepare a powdered product. Casein is obtained through ultrafiltration or pH regulation, heat solidified and reacted with hydrolase to prepare casein phosphate polypeptide. The process is said to greatly lower production costs.

Chinese Patent No. 1557340 (also to Gao Chunping) describes a method of preparing a high bioreactivity growth factor and immunoglobulin from bovine colostrum. The method involves collecting colostrum 72 hours after parturition, defatting the colostrum through centrifugation, acidifying the solution, heating to solidify casein, centrifugally filtering or filtering the solution with cloth to eliminate casein, diluting the resulting solution, collecting the supernatant, concentrating with low molecular weight ultrafiltration membranes, and processing further in order to produce a dry powder preparation, a spray preparation, and the like. The product is intended for use in the treatment of various bacterial and viral infections.

U.S. Pat. No. 6,875,459 (Kopf et al.) discloses a method and apparatus for separation of milk, colostrum and whey components. In a preferred embodiment, the apparatus and method employ cross-flow filtration, chromatography and fermentation to separate the components of milk, colostrum and whey. The apparatus and method allow the extraction of immunoglobulins, among other factors.

European Patent No. 711171 (Laato et al.) describes a method for the improvement of wound healing in mammals, including humans, by using a colostral fraction. The colostral fraction is prepared by subjecting colostrum, from which part of the fat and cellular debris have been removed by conventional methods such as centrifugation, to ultrafiltration by using a membrane having a cutoff of 100 kDa and recovering the filtrate. The method for promoting wound healing consists of administering the colostral fraction locally.

PCT Publication No. WO 9811910 describes the use of a composition containing at least one compound with Growth Factor-like activity for the prevention or treatment of a gastrointestinal condition that is characterized at least partially by damage to epithelial cells and caused by the administration of a non-steroidal anti-inflammatory drug. Compositions for use in the invention may contain an IGF (e.g. IGF-1 or 2), a transforming growth factor (e.g. TGF1, TGF2 or TGF3), a keratinocyte growth factor, a fibroblast growth factor and/or a platelet-derived growth factor. The compositions containing the TGFs are preferably, though not exclusively, derived from colostrum. Similarly, PCT Publication No. WO 9811904 describes the use of colostrum or a derivative thereof for the prevention or treatment of a gastrointestinal condition that is characterized at least partially by damage to epithelial cells and caused by the administration of a non-steroidal anti-inflammatory drug. Derivatives suitable for use include ultra-filtered or microfiltered fractions of colostral whey (colostrum from which casein proteins have been removed), which are said to contain more concentrated Growth Factors relative to remaining colostral proteins and nutrients. Colostral whey may be used in liquid form (which may be defatted if desired) or may be further treated (such as being spray dried).

Other methods for the extraction of growth factors are known in the art, but surprisingly, no process appear to exist for deliberately and simultaneously isolating growth factors with highly disparate molecular weights. In addition, a number of methods rely on temperature conditions that have the effect of destroying the activity of the growth factors that are sought to be extracted.

There is therefore a need for a method of isolating growth and differentiating factors from colostrum that permits the separation of a great number of these factors (or "pools" of factors) in a manner that is efficient, reproducible and non-deleterious to their activities.

SUMMARY OF THE INVENTION

In accordance with the present invention, there is provided a novel process for isolating growth and differentiating factors from colostrum. More specifically, this process is characterized by maturation steps (controlled mild acid hydrolysis) and physical steps (molecular filtration) which optimize recovery of measured growth factors and their ability to entice a response on human cells.

In contrast to processes that are known in the art, the process of the present invention is neither performed at boiling temperatures. What results from this process are novel filtrate "pools" containing factors that are active on human cells, even if the colostrum is of bovine origin.

In one preferred embodiment, the process includes:
Diluting the colostrum and subjecting it to partial hydrolysis by adjusting the pH to about 3.75-3.85;
vortexing the resulting colostral solution 60 minutes (30-90 minutes);
adjusting the pH of the colostral solution to about 4.52-4.55;
centrifuging the new colostral solution, and setting aside the resulting supernatant; and
running the supernatant through a filtration system comprising one or more filtration columns (ceramic membranes) in order to obtain a fraction containing pools of growth and differentiating factors,
all the while ensuring that the reaction temperature never exceeds 38° C.

In another embodiment, the process further comprises lyophilizing the pools of derived growth and differentiating factors.

Generally, the process includes a filtration system which is comprised of one or more filtration columns selected from the following filtration sizes: 0.2 µm, 300 kDa, 150 kDa, 50 kDa, 15 kDa and 5 kDa. More specifically, and depending on the content and concentration of pooled growth and differentiating growth factors that are sought, the filtration system is selected from one of the following: a 0.2 µm column; a 300 kDa column; a 150 kDa column; a 50 kDa column; a 15 kDa column; a 0.2 µm column linked with a 150 kDa column; a 0.2 µm column linked with a 15 kDa column; and a 150 kDa column linked with a 15 kDa column.

The invention further includes colostral fractions isolated from the process of the present invention. Such fractions may include one or more fractions selected from the following: LP1, LP2, LP3, LP4, LP5, LP1-LP3, LP1-LP5 and LP3-LP5 (see the compositions of these fractions in Table 5). Depending on the application, these fractions may be used in their native form or they may be combined with an excipient or carrier.

Advantageously, this process allows the derivation and isolation of growth and differentiating factors, with the result that a number of factors with highly disparate sizes (or molecular weights) can be separated in pools from one another and used in select and varied ways, such as in cosmetic, cosmeceutical, nutraceutical, dermatological, pharmaceutical, medical and veterinary applications.

Other objects, advantages and features of the present invention will become apparent upon reading of the following non restrictive description of preferred embodiments thereof, given by way of example only with reference to the accompanying drawings.

BRIEF DESCRIPTION OF THE DRAWINGS

FIG. 2: Growth factors found in colostral fractions.

FIG. 3: Human ELISA test results for growth factors found in colostral fractions.

FIG. 18: Wound (dermal) thickness 5 after 7 days and 14 days resulting from LP1-LP3, LP1-LP5 and LP3-LP5.

DESCRIPTION OF THE PREFERRED EMBODIMENTS

Figure 1A:
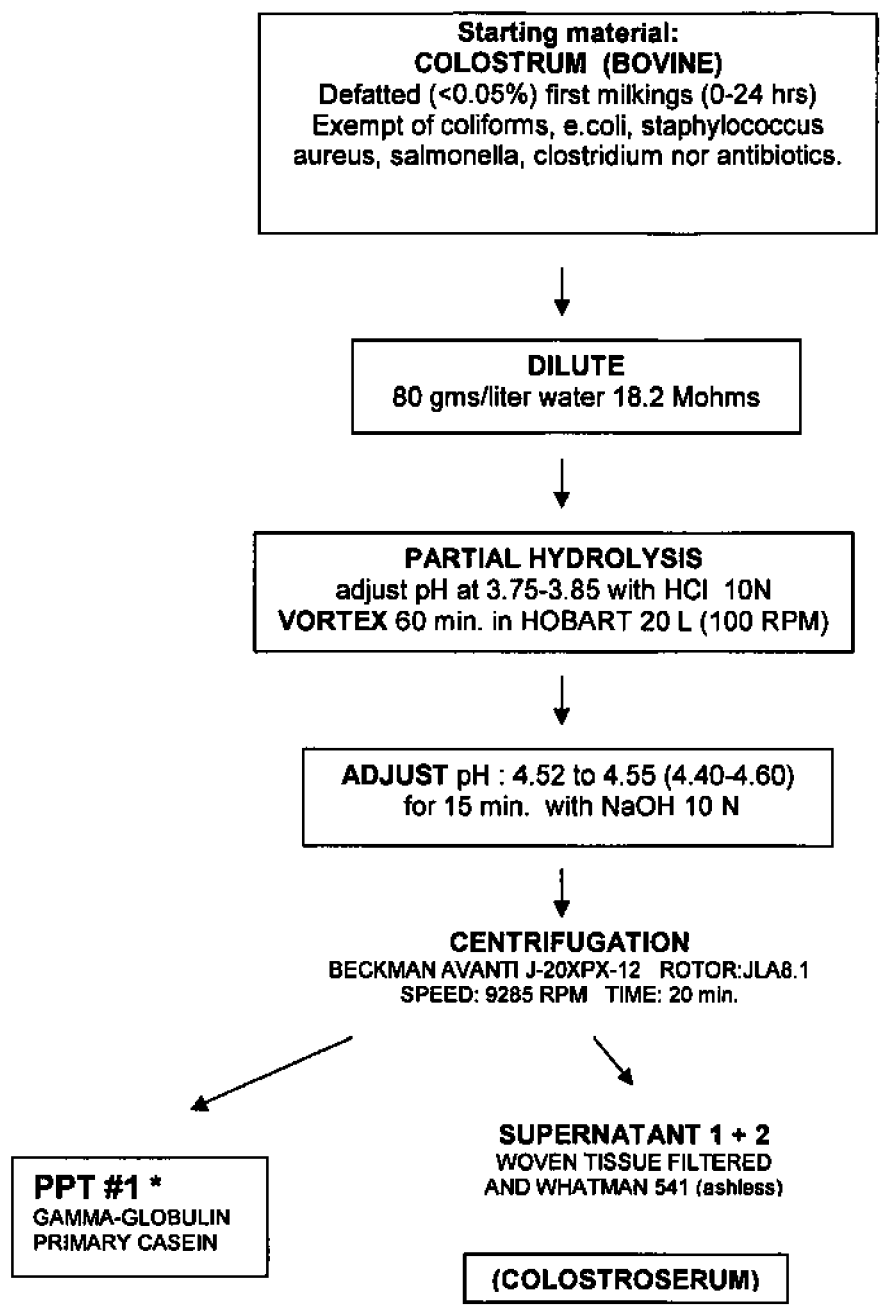
FIG. 1: Schematic view of the process steps for the isolation of growth factors from colostrum, including (A) controlled mild acid hydrolysis and (B) molecular filtration.

Definitions: Unless defined otherwise, all technical and scientific terms used herein have the same meaning as commonly understood by one of ordinary skill in the art to which this invention belongs.

"Cosmeceutical": A cosmetic product claimed to have medicinal or drug-like benefits. Cosmeceutical products are marketed as cosmetics, but reputedly contain biologically active ingredients. Examples include anti-wrinkle skin creams with ingredients such as alpha lipoic acid and dimethylaminoethanol.

"Brush cell": A brush cell has rootlet like projections as a tuft that form squat microvilli with filaments that stretch into the cell's cytoplasm; about 120-140 microvilli may be found on each cell, and the cell has a skewed or tilted position in tissue sections. Brush cells have been identified in the gastrointestinal (about 0.3% cells) and respiratory tracts, Identification of brush cells has relied primarily on morphology with electron microscopy; they have a distinctive pear shape with a wide base, and a narrow microvillous apex. The function of brush cells is to activate the digestion and absorption of sugars, amino acids and small chain carbohydrates in the bowel.

(See the following Internet page from the National Heart, Lung and Blood Institute: http://www.nhlbi.nih.gov/meetings/workshops/brush-cell.htm.)

"Digestive epithelium": The digestive tube, which is comprised of comprised of the oral cavity (mouth), pharynx (throat), esophagus, stomach, small intestine, large intestine, and rectum is lined by a simple (1 cell thick) epithelium that is continuous at either end with the epidermis of the skin. This digestive epithelium is a mucosa, i.e. an epithelium that secretes watery mucus for the purpose of lubrication. (See http://www.sbs.utexas.edu/shankland/lc11dig1.htm)

The following is a list of all growth and differentiating factors detected by human ELISA tests built in with factors of human origin as standards. (See also FIG. 3.)

BMP-2: bone morphogenic protein 2
BMP-4: bone morphogenic protein 4
EGF: epidermal growth factor
FGF-2: (basic) fibroblast growth factor basic
FGF-4: fibroblast growth factor 4
HGF: hepatocyte growth factor
IGF-1: insuline-like growth factor 1
IGFBP-1: insuline-like growth factor binding protein 1
IGFBP-3: insuline-like growth factor binding protein 3
KGF (FGF-7): keratinocyte growth factor (fibroblast growth factor-7)
PDGF-AA: platelet-derived growth factor-AA
PDGF-AB: platelet-derived growth factor-AB
PDGF-BB: platelet-derived growth factor-BB
PLGF: placenta growth factor
SCF: stem cell factor c-kit ligand
TGF-α: transforming growth factor alpha
TGF-β1: activated transforming growth factor beta 1
TGF-β2: activated transforming growth factor beta 2
TNFα: tumor necrosis factor alpha
TNFβ: tumor necrosis factor beta
VEGF: vascular endothelial growth factor

EXAMPLE 1

Isolation of Growth and Differentiating Factors from Commercially Available Bovine Colostrum The process of the invention, shown schematically in FIGS. 1 (A) & (B), will now be described.

It should be appreciated here that while this process is specifically described for use with colostrum, substitutes for colostrum, namely other milks and milk products, may also be used. The efficiency of the process is believed to be enhanced with colostrum, because colostral milk contains a higher concentration of growth and differentiation factors than other milks and milk products. Colostral substitutes—filter sterilized milk, modified milk (i.e., milk from which the fatty constituents have been wholly or partially removed, with or without the addition of vitamins or solid elements derived from milk), enriched milk (i.e., enriched with non-fat solids), vitaminized milk (milk with vitamins added), and lacto-serum—may also be used as starting materials since they are known to contain growth and differentiation factors of a similar nature. However, not all the factors will be found in milk, and then, not in the same concentration as in colostrum. When using a colostral substitute, it will be necessary to modify the process slightly to maximize the yields of growth and differentiation factors. Such modifications should be within the purview of one of skill in the art.

1. Preliminary Preparation

When starting with a lyophilized colostral preparation (freeze dried colostrum exempt of fat, coliforms and antibiotics) it has been found that the best way to reconstitute colostrum is to dissolve 80 g per liter of water (18.2 Mega Ohms).

The best pH for extraction is between about 3.75 and 3.85. The colostrum is adjusted to this pH (with a 10 N HCl solution, for example) and then placed in an agitator (Hobart™), at the first speed for 60 minutes. The pH of the solution is readjusted, with NaOH 10 N, to a pH of about 4.52-4.55 and the solution agitated for another 15 minutes before being centrifuged for 20 minutes at 9285 G. The best results were observed using a Beckman™ Avanti J-20XPX-12 with rotor JLA 8.1 centrifuging 6 liters at a time for 20 minutes at 9285 G.

The combined precipitates are dissolved in water for re-extraction (12 liters of 18.2 Mega Ohms for every kg of precipitate) and centrifuged again for about 20 minutes at 9285 G. The supernatants from each bottle are added to the pooled supernatant (1) from the first centrifugation. The final pH of the solution sometimes needs to be readjusted as it will be 4.35-4.40 instead of the 4.50-4.65 required for optimal results.

The solution is now ready for filtration and lyophilization, as described below.

2. Filtration Using TAMILAB® Filter System

Using the solution obtained in step 1, filtration is conducted by passing the supernatant through progressively smaller filtration columns, or molecular sieves. The choice of molecular sieve will depend on the fraction that is sought. As shown in Table 1, these fractions are identified as LP1 to LP5, depending on the filtration column selected.

TABLE 1

Correspondence between Filtration Column and Fraction

| Filtration Size | Retention | Fraction |
|---|---|---|
| 0.2 μm | 5 kDa | LP1 |
| 300 kDa | 5 kDa | LP2 |
| 150 kDa | 5 kDa | LP3 |
| 50 kDa | 5 kDa | LP4 |
| 15 kDa | 5 kDa | LP5 |

In accordance with one embodiment of the present invention, in order to obtain fraction LP3 (150 kDa-5 kDa), a first filtration is performed using a 0.20 μm column. A column of this size will eliminate unwanted factors quickly before the supernatant is passed through the 150 kDa column, which is the column that is suitable for the LP3 fraction.

Moreover, in-between fractions may also be generated. For example, fraction LP3 may be filtered on a 50 kDa molecular sieve (used to obtain LP4). The result will be a retentate having a cutoff molecular weight of 150 kDa to 50 kDa (LP3-LP4). Similarly, LP4 may be filtered on a 15 kDa molecular sieve (used to obtain LP5). The result will be a retentate having a cutoff molecular weight of 50 kDa to 15 kDa (LP4-LP5).

As may be seen in Table 2, certain in-between fractions or pools were found to be especially interesting. These are LP1-LP3, LP1-LP5 and LP3-LP5. To prepare the LP1-LP3 fraction or pool, the solution resulting from Step 1, above, is run through a column having a 0.2 μm cutoff and then through a column having a 150 kDa cutoff. Similarly, to prepare the LP1-LP5 fraction or pool, the solution resulting from Step 1, above, is run through a column having a 0.2 μm cutoff and then through a column having a 15 kDa cutoff. Likewise, to prepare the LP3-LP5 fraction or pool, the solution resulting from Step 1, above, is run through a column having a 150 kDa cutoff and then through a column having a 15 kDa cutoff.

3. Lyophilization

This operation must be done very carefully in order to maximize efficiency. The different fractions are divided into samples of 2.5 liters per tray on lyophilizer FTS and frozen at about −35° C. This method permits rapid freezing without liquid nitrogen.

In a FTS tray lyophilizer the tray must be placed one at a time at 4° C. without vacuum then frozen to −35° C. before applying vacuum (10-100 mThors) at −80° C. to −85° C. for approximately 36-48 hours; the lyophilized samples, once in the form of a fine powder (250-500 μm) are ready for encapsulation or ready to be pooled and conserved in storage bags (sterile freezer bags) at a temperature of approximately −18° C. to −20° C.

Using the process described above, it is possible to isolate growth and differentiating factors from colostrum. FIG. 2 shows the growth factors found in the following fractions, as verified through human ELISA testing: LP1, LP2, LP3, LP4, LP5, LP1-LP3, LP3-LP5 and LP1-LP5.

FIG. 3 reveals the quantities of certain of the growth factors identified in FIG. 2. The quantities, measured through human ELISA, are per kg of colostrum.

Table 2 shows the quantity of isolated product per fraction for colostrum (1 kg; dry matter basis).

TABLE 2

Quantity of Isolated Product per Fraction for Colostrum

| Fraction | Filter | Weight (g/Kg) |
|---|---|---|
| LP1 | F 0.2 μm-R 5 kDa | ≈90 |
| LP2 | F 300 kDa-R 5 kDa | ≈55 |
| LP3 | F 150 kDa-R 5 kDa | ≈35 |
| LP4 | F 50 kDa-R 5 kDa | ≈25 |
| LP5 | F 15 kDa-R 5 kDa | ≈20 |
| LP1-LP3 | F 0.2 μm-R 150 kDa | ≈50 |
| LP1-LP5 | F 0.2 μm-R 15 kDa | ≈70 |
| LP3-LP5 | F 150 kDa-R 15 kDa | ≈30 |

EXAMPLE 2

Isolation of Growth and Differentiating Factors from Natural Colostrum (from Dairy Cows)

1. Preliminary Preparation

Frozen colostrum is thawed (storage temperature is −20° C.) then centrifuged 6 liters at a time at 20° C. The layer of butter and other residues are filtered first through cheesecloth and then through a Whatman™ 541 ashless filter. A thorough removal of this layer of fat will facilitate filtration and enhance the overall isolation of the growth and differentiating factors.

This preliminary filtration is followed by acid extraction at a pH of about 3.75-3.85. It is convenient to use a 10 N HCl solution for this purpose. If needed, water can be added to the supernatant (to a maximum of about 10%) in order to increase the fluidity of the supernatant for extraction. This greatly enhances filtration on the TAMILAB® system of columns (0.20 μm, 300 kDa, 150 kDa, 50 kDa, 15 kDa and 5 kDa), as will be described below.

The solution is now ready for filtration and lyophilization, as described in Example 1.

NB: As with Example 1, it should be appreciated here that while this process is specifically described for use with colostrum, substitutes for colostrum, namely other milks and milk products, may also be used. When using a colostral substitute, it may be necessary to modify the process slightly to maximize the yields of growth and differentiation factors. Such modifications should be within the purview of one of skill in the art.

EXAMPLE 3

Preferred Isolation Method for LP1-LP5

Figure 1:
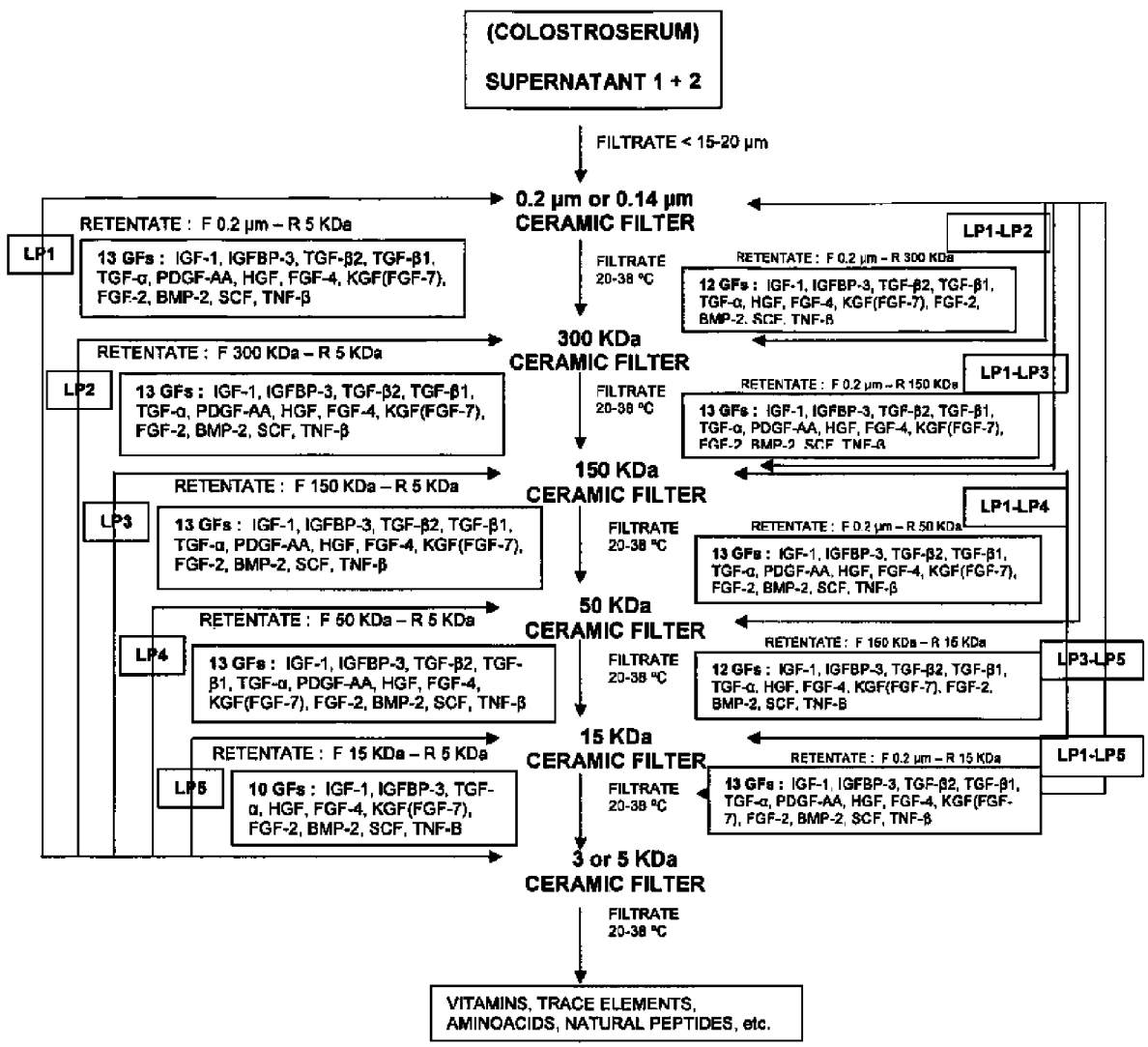

The following process is based on that shown schematically in FIGS. 1(A) and (B).
1. Isolation
1.1 Starting with a lyophilized colostral preparation (freeze dried colostrum exempt of fat, coliforms, *E. coli, S. aureus*, salmonella, clostridium and antibiotics, colostrum is reconstituted by dissolving 1000 g of raw colostrum per 12 liters of water (0.2 μm filtered), placed in a blending tank (Hobart™) and agitated for 15 minutes;
1.2 The pH is adjusted to between 3.75 and 3.85 with a 10 N HCl solution and run at ≈400 rpm for 60 minutes;
1.3 The pH of the solution is readjusted with a 10N NaOH solution, to a pH of about 4.50-4.60, and the solution agitated for another 15 minutes at the same speed;
1.4 The solution is centrifuged for 20 minutes at about 9285 G, 18° C. using a Beckman™ Avanti J-20XPX-12 with rotor JLA 8.1, centrifuging 6 liters at a time;
1.5 The supernatant is filtered on Whatman 541 Ashless filter and store in a 25 liter bottle at 4° C. until all centrifugation is completed and move on to filtration; and
1.6 The total quantity of quantity of solution to be filtered is between 20.5 to 21.5 liters.
2. Filtration Using TAMILAB® Filter System
2.1 Before starting filtration, the machine is rinsed by running 7 liters of alcohol (70%) through the system, letting 2 liters out and letting stand for 5 minutes before draining 5 liters;
2.2 The machine is rinsed again by running 5 liters of filtered water (0.2 μm) through the system, letting 2 liters out and draining from the system;
2.3 The solution from in step 1 is filtered by passing the supernatant through two 0.2 μm Dahlia ceramic columns with 1000 cm$^2$ surface (CéRAM from TAMI Industries);
2.4 The temperature of the solution in the filtration system should never exceed approximately 37° C. (if the temperature exceeds 37° C., the machine should be stopped for 15 minutes while the tank is refrigerated);
2.5 The filtration process is stopped at 4 liters less than the total starting quantity, the filtrate kept and stored at 4° C. until the next day and the system thoroughly drained;
2.6 9.5 liters of filtered water are run through the system (0.45 μm) heated at 100° C. with 500 ml of 10 N NaOH until it reaches 50-70° C.;
2.7 5 liters of filtered water are added and run until the tank is empty, and then drained from the system;
2.8 9 liters of filtered water are run through the system (0.45 μm), heated at 60-70° C. with 1 liter of 10N HCl, stopped and drained from the system;
2.9 7 liters of filtered water (0.2 μm) and 3 liters are run through and drained from the system;
2.10 7 liters of alcohol (70%) are added and 2 liters run through and the system drained;
2.11 0.2 μm columns are exchanged for 15 kDa columns;
2.12 7 liters of alcohol (70%) are run through the system, letting 2 liters out and letting stand for 5 minutes before draining the system;
2.13 The system is rinsed by running 5 liters of filtered water (0.2 μm) through it, letting 2 liters out;
2.14 The 0.2 μm filtrate is passed through two 15 kDa Dahlia ceramic columns with 1000 cm$^2$ surface (CéRAM from TAMI Industries);
2.15 The temperature of the filtration system should never exceed 37° C. (if it does, the machine should be stopped for 15 minutes);
2.16 The filtration process should be stopped at 3.5 liters less than the total starting quantity;
2.17 The system should be drained and the retentate kept;
2.18 The retentate should be centrifuged at 9285 G for 20 minutes;
2.19 The supernatant is ready for lyophilisation; it is stored at 2-4° C. until ready for processing;
2.20 To clean the filtering machine, points 2.6 to 2.10 are repeated;
2.21 In order to keep the system germ free, the process should always be finished with adequate cleaning procedures and the columns stored in alcohol.
3. Lyophilization
3.1 Using a FTS tray lyophilizer, the supernatant is processed according to the instructions for this equipment;
3.2 After the lyophilization is complete, the powder is passed through a 250 or 500 μm sieve under sterile environment;
3.3 The powder is conserved in sterile 50 ml centrifugation tubes, 20 grams per tube and stored at a temperature of about −16° C. to −24° C.;
3.4 The powder could be irradiated up to 8 kGy without loss of activity on human cells; and
3.5 The powder is stored at a temperature of about −16° C. to −24° C.

EXAMPLE 4

Isolation Results for Growth Factors IGF-1 and TFG-$\beta_2$ (after Partial Hydrolysis)

Growth Factors IGF-1 and TFG-$\beta_2$ were quantified in 2.5 ml fractions (hydrogenated, pH 3.9 colostrum) that were purified on HPLC. Tables 3 and 4 show the results for growth factors IGF-1 and TFG-$\beta_2$, respectively.

TABLE 3

Quantification of IGF-1 in Retentate 21

| Sample (MW/% retentate) | No. | Concentration (mg/ml) | O.D. | Correction Factor * Dilution factor | Quantity IGF-1 (ng/ml) | Specific Activity (μg/g powder) |
|---|---|---|---|---|---|---|
| Fraction 2 (>1400 kDa/2.8%) | X1 | 20.0 | 0.001 | 100 * 1 | N/A | N/A |
| Fraction 3 (1400 kDa/5.6%) | X2 | 20.0 | 0.005 | 100 * 1 | N/A | N/A |

TABLE 3-continued

Quantification of IGF-1 in Retentate 21

| Sample (MW/% retentate) | No. | Concentration (mg/ml) | O.D. | Correction Factor * Dilution factor | Quantity IGF-1 (ng/ml) | Specific Activity (µg/g powder) |
|---|---|---|---|---|---|---|
| Fraction 4 (950 kDa/4.8%) | X3 | 20.0 | 0.007 | 100 * 1 | N/A | N/A |
| Fraction 5 (680 kDa/4.3%) | X4 | 20.0 | 0.002 | 100 * 1 | N/A | N/A |
| Fraction 6 (490 kDa/4.0%) | X5 | 20.0 | 0.001 | 100 * 1 | N/A | N/A |
| Fraction 7 (350 kDa/3.2%) | X6 | 20.0 | 0.002 | 100 * 1 | N/A | N/A |
| Fraction 8 (250 kDa/4.1%) | X7 | 20.0 | 0.002 | 100 * 1 | N/A | N/A |
| Fraction 9 (180 kDa/2.8%) | X8 | 19.7 | −0.001 | 100 * 1 | N/A | N/A |
| Fraction 10 (133 kDa/16.6%) | X9 | 20.0 | 0.002 | 100 * 1 | N/A | N/A |
| Fraction 11 (96 kDa/11.3%) | X10 | 20.1 | 0.005 | 100 * 1 | N/A | N/A |
| Fraction 12 (70 KDa/5.5%) | X11 | 20.0 | 0.061 | 100 * 1 | 48.4 | 2.42 |
| Fraction 13 (>45 kDa/2.8%) | X12 | 20.0 | 0.231 | 100 * 1 | 125.1 | 6.26 |
| Fraction 14 (35 kDa/7.4%) | X13 | 20.0 | 0.081 | 100 * 1 | 58.5 | 2.93 |
| Fraction 15 (26 kDa/4.1%) | X14 | 20.0 | 0.058 | 100 * 1 | 46.9 | 2.35 |
| Fraction 16 (20 kDa/3.0%) | X15 | 20.0 | 0.056 | 100 * 1 | 45.9 | 2.29 |
| Fraction 17 (13 kDa/1.9%) | X16 | 20.0 | 0.113 | 100 * 1 | 74.7 | 3.73 |
| Fraction 18 (10 kDa/1.6%) | X17 | 20.0 | 0.146 | 100 * 1 | 91.3 | 4.57 |
| Fraction 19 (7 kDa/0.7%) | X18 | 10.0 | 0.257 | 100 * 1 | 147.3 | 14.73 |

TABLE 4

Quantification of TGF-$\beta_2$ from Retentate 21-CLAR in Fractions 2 to 25 purified with HPLC

| Sample (MW/% retentate) | No. | Concentration (mg/ml) | O.D. | Over-estimation O.D − 0.120 | [a]Correction Factor * Dilution factor | [b]corrected TGF-$\beta_2$ Quantity (pg/ml) | Specific Activity (µg/g powder) |
|---|---|---|---|---|---|---|---|
| Fraction 2 (>1400 Kda/2.0%) | Xl | 9.9 | 0.948 | 0.828 | 7.8 * 1 | 4161.1 | 420.32 |
| Fraction 3 (1400 Kda/4.7%) | X2 | 10.1 | 1.061 | 0.941 | 7.8 * 1 | 4747.1 | 470.01 |
| Fraction 4 (950 Kda/3.1%) | X3 | 9.8 | 1.607 | 1.487 | 7.8 * 1 | 7604.8 | 776.00 |
| Fraction 5 (680 Kda/2.6%) | X4 | 9.8 | 3.258 | 3.138 | 7.8 * 1 | 16410.2 | 1674.52 |
| Fraction 6 (490 Kda/2.3%) | X5 | 10.0 | 3.460 | 3.340 | 7.8 * 1 | 17499.2 | 1749.92 |
| Fraction 7 (350 Kda/2.2%) | X6 | 10.1 | 3.013 | 2.893 | 78 * 1 | 15092.3 | 1494.29 |
| Fraction 8 (250 Kda/2.4%) | X7 | 9.9 | 1.472 | 1.352 | 7.8 * 1 | 6894.7 | 696.44 |
| Fraction 9 (180 Kda/7.0%) | X8 | 10.0 | 0.372 | 0.252 | 7.8 * 1 | 1222.2 | 122.22 |
| Fraction 10 (l33 Kda/12.2%) | X9 | 10.0 | 0.435 | 0.315 | 7.8 * 1 | 1538.0 | 153.80 |
| Fraction 11 (96 Kda/7.3%) | X10 | 9.9 | 1.725 | 1.605 | 7.8 * 1 | 8227.0 | 831.01 |
| Fraction 12 (70 Kda/3.9%) | X11 | 10.2 | 2.314 | 2.194 | 7.8 * 1 | 11351.6 | 1112.90 |
| Fraction 13 (50 Kda/3.6%) | X12 | 9.9 | 0.625 | 0.505 | 7.8 * 1 | 2500.7 | 252.59 |
| Fraction 14 (35 Kda/7.3%) | X13 | 9.9 | 0.117 | −0.003 | 7.8 * 1 | N.A. | N.A. |

TABLE 4-continued

Quantification of TGF-$\beta_2$ from Retentate 21-CLAR
in Fractions 2 to 25 purified with HPLC

| Sample (MW/% retentate) | No. | Concentration (mg/ml) | O.D. | Overestimation O.D − 0.120 | [a]Correction Factor * Dilution factor | [b]corrected TGF-$\beta_2$ Quantity (pg/ml) | Specific Activity (µg/g powder) |
|---|---|---|---|---|---|---|---|
| Fraction 15 (26 Kda/4.8%) | X14 | 10.2 | 0.115 | −0.005 | 7.8 * 1 | N.A. | N.A. |
| Fraction 16 (20 Kda/3.0%) | X15 | 10.1 | 0.131 | 0.011 | 7.8 * 1 | N.A. | N.A. |
| Fraction 17 (13 Kda/2.6%) | X16 | 10.2 | 0.128 | 0.008 | 7.8 * 1 | N.A. | N.A. |
| Fraction 16 (10 Kda/1.7%) | X17 | 9.9 | 0.115 | −0.005 | 7.8 * 1 | N.A. | N.A. |
| Fraction 19 (7 Kda/1.2%) | X18 | 10.0 | 0.115 | −0.005 | 7.8 * 1 | N.A. | N.A. |
| Fraction 20 (5 Kda/1.2%) | X19 | 10.0 | 0.116 | −0.004 | 7.8 * 1 | N.A. | N.A. |
| Fraction 21 (3.5 Kda/0.6%) | X20 | 10.0 | 0.090 | −0.030 | 7.8 * 1 | N.A. | N.A. |
| Fraction 22 (2.5 Kda/0.8%) | X21 | 10.0 | 0.098 | −0.022 | 7.8 * 1 | N.A. | N.A. |
| Fraction 23 (2 Kda/0.3%) | X22 | 10.0 | 0.086 | −0.034 | 7.8 * 1 | N.A. | N.A. |
| Fraction 24 (1.5 Kda/0.2%) | X23 | 10.0 | 0.126 | 0.008 | 7.8 * 1 | N.A. | N.A. |
| Fraction 25 (1 Kda/0.3%) | X24 | 10.0 | 0.092 | −0.028 | 7.8 * 1 | N.A. | N.A |

Discussion

The results in Tables 3 and 4 are but two examples showing the specific activity of the pools of factors derived using the process of the present invention. Partial hydrolysis converts many factors from their inactive (or "pro") forms (>450 kDa) to their active forms. Significantly, these factors, which are present in pools in the various fractions, as verified through human ELISA testing (FIG. 3), have been found to be active on human cells.

EXAMPLE 5

Effect on Cell Behavior of a Variety of Purified Fractions

1. Objectives of the Study

The objectives of the study were to evaluate the effect on cell behavior of a variety of fractions purified with the process of the present invention. The pools tested were termed LP1, LP2, LP3, LP4, LP5, LP1-LP3, LP3-LP5 and LP1-LP5. The proliferation and growth of human fibroblasts as well as their collagen synthesis were investigated in vitro in order to select optimal pools for further study. In addition, some studies were also performed with human vascular endothelial cells.

2. Materials and Methods 2.1. Cells

Human fibroblasts, stored in liquid nitrogen, and derived from foreskin of young were used at passages 3-8. Fibroblasts were grown in Dulbecco's modified Eagles medium with 5% fetal bovine serum (FBS). Ascorbic acid and β-aminopropionitrile were added to the cultures dedicated to the collagen synthesis assessment.

Human vascular endothelial cells, stored in liquid nitrogen and derived from umbilical veins (HUVECs), were used at passages 3-4. HUVECs were grown on gelatin-adsorbed culture dishes in Medium 199 containing 10% FBS, L-glutamine (2 mM) and endothelial cells growth supplement (ECGS at 20 µg/ml). To test the pools, serum-free Medium 199 was used with ECGS and L-glutamine to permit cell survival. In a pilot experiment, endothelial cells died in less than 24 hrs when grown in culture without ECGS and serum.

2.2. LP Pool Concentrations

In the first set of experiments, LP pools were diluted to final concentrations of 0.1, 1.0, 10 mg/ml. In the following sets of experiments, the final concentrations tested were 0.33, 1.0, and 3.3 mg/ml. These conditions were compared to negative control cultures free of serum. In some cases, serum-supplemented medium was used in positive control cultures.

2.3. Proliferation Test (Cyquant® Assay from Molecular Probes)

Cells were seeded in wells of 24 multiwell plates at a density of $5 \times 10^3$ fibroblast/well and a density of $1 \times 10^4$ endothelial cells/well and grown for 6-24 hrs to allow cell adhesion in the presence of serum (5% for fibroblasts, and 10% for endothelial cells). At time zero, medium was removed and cells were rinsed twice with Hank's balanced salt solution (HBSS), then replaced by culture serum-free medium containing the LP pool to be tested at different concentrations. Control cultures were grown in parallel. After 12 or 24 hours of growth without changing medium, medium was removed, and the wells were rinsed twice in PBS. Multiwell plates were frozen at −70° C. Two hours later, plates were thawed, the lysis buffer (solutions A and B, provided with the kit, revealing fluorescent solutions) was added with an incubation of 3-5 minutes, then fluorescence was read in a cytoplate with a BioTek FL-600 fluorometer at 480 nm excitation and 520 nm emission.

2.4. Cell Growth (Hoechst)

Cells were seeded in wells of 24 multiwell plates at a density of $1 \times 10^4$ fibroblast or endothelial cells/well and grown overnight (or 24 hrs in the first set of experiment) to allow cell adhesion in the presence of serum (5% for fibroblasts, and 10% for endothelial cells). The next day (time zero), medium was removed and cells were rinsed twice with HBSS, then replaced by culture serum-free medium containing the LP pool to be tested at different concentrations. After 72 hours of growth without changing medium, medium was removed, and the wells were rinsed twice in PBS. Then, PBS was replaced by a 200 μl saline-sodium citrate buffer (SSCI) solution containing 0.1% SDS, and incubated for 1 hour at 37° C. Twenty (20) μl of Hoechst 33258 solution (at 1 mg/ml) was added to the SSCI solution. After agitation (up-down), fluorescence was read in a cytoplate at 340 nm excitation and 460 nm emission with a sensitivity set at 100-120.

In parallel, incrementing cell density was established, incubated with Hoechst 33258 solution (at 1 mg/ml), then fluorescence was read to perform a standard curve in which the cell number is plotted against the optical density.

2.5. Statistic Analyses

One Way Analysis of Variance was used for the statistical analysis of quantitative data, with a p value ≦0.05. Bonferroni t-test method was used for all pairwise comparison procedures.

2.6. Collagen Synthesis in Monolayer Fibroblast Cultures

Cells were seeded in wells of 24 multiwell plates at a density of $1 \times 10^5$ fibroblast/well and grown overnight to allow cell adhesion in the presence of serum (5%), ascorbic acid (10 μg/ml) and β-aminoproprionitrile (10 μg/ml). The next day (time zero), medium was removed, rinsed with PBS, and cells were exposed to medium containing LP pools, and radioactive proline ($^{14}C$ or $^3H$ proline). Control cultures were run in parallel. Cultures lasted for 7 days to allow collagen synthesis and deposition, for which fresh medium containing LP pools and radioactive proline was changed every other day. At medium changes, media of each condition were collected and pooled (i.e., soluble collagen). At the end of the 7 day culture period, cells and matrix were pooled (i.e., cellular, insoluble and deposited collagen), separately of the medium pools (i.e., soluble collagen). Matrix-cells and media were promptly diluted in a protease cocktail inhibitor solution. Matrix-cell pools were counted on a scintillation counter, whereas medium pools were dialyzed to remove any free radioactive proline, then counted.

2.7. Cell Cultures in 3-D Fibrin Gel and Collagen Synthesis/Deposition

Fibrin gel was used instead of collagen gel in order to investigate the collagen/deposition by fibroblasts, since collagen itself is known to inhibit collagen synthesis. Moreover, fibrin represents the primary extracellular matrix during wound healing. A 3 mg/ml fibrinogen solution was mixed with $5 \times 10^4$ fibroblasts/ml and polymerized by thrombin in the wells. The fibrin gels were then covered with culture medium containing the different LP pools, and radioactive proline. The method to analyze collagen synthesis and deposition was similar to that described earlier in Section 2.6, above.

3. Results 3.1. Fibroblast Proliferation

Proliferation was measured at 12 and 24 hrs of cultures in the presence of LP pools with incrementing concentrations.

At 24 hours, 1 mg/ml LP1 and LP1-LP3 induced a statistically significant higher value compared to the other LPs and control culture with no serum (not shown). At 10 mg/ml, the values with LP1 were significantly higher than those with LP1-LP3 at the same concentration. The latter was not different statistically with 10 mg/ml LP2, but different with 10 mg/ml LP3, LP4 and LP5. The values of LP1 were similar at 1 and 10 mg/ml. The values between 1 and 10 mg/ml of LP1-LP3 and LP2 were also similar. The values with 1 and 10 mg/ml LP1, LP2 and LP1-LP3 were significantly higher than those at 0.1 and 1 mg/ml. The values of LP4 and LP3 were not significantly different. High doses of LP5 induced a significant inhibition compared to control and the other LP pools at 10 mg/ml.

At 12 hrs (not shown), the values of cell proliferation at 0.33, 1 and 3.3 mg/ml of LP1-LP3 was statistically higher than the other conditions, except with 3.3 mg/ml LP-2 which was similar to LP1-LP3. However, the values with 3.3 mg/ml LP2 were not different than LP1, LP3, LP4 and LP5 at the same concentration.

3.2. Fibroblast Growth

The first assay was performed with 0.1, 1.0 and 10 mg/ml of LP pools (not shown). There was a statistically significant increase in the presence of LP1-LP3 at 1 and 10 mg/ml and between 1 and 10 mg/ml LP1-LP3. LP1-LP3 did not reach the number of cells found in the control cultures in serum-supplemented medium, which was 1.5-fold increase.

A significantly higher number of cells was found in the presence of 10 mg/ml LP1, LP2, LP3 and LP4 compared to those pools at lower doses, control without serum, and to 10 mg/ml LP5. The presence of LP5 resulted in a significant inhibition at the highest dose (10 mg/ml).

Figure 4:
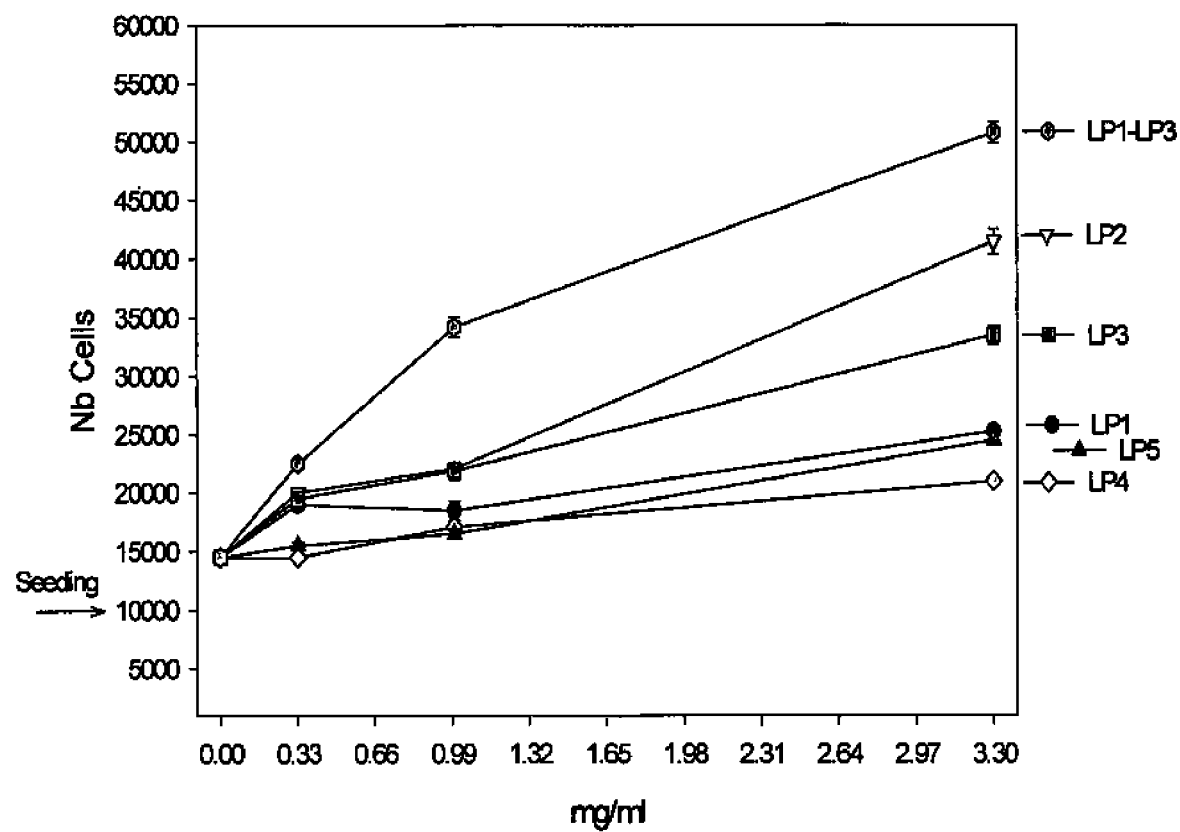
FIG. 4: Fibroblast growth (Hoechst) during 72 hr exposure.

A second set of experiments was performed with 0.33, 1.0 and 3.3 mg/ml of LP pools (FIG. 4). The numbers of cells in the presence of 1.0 and 3.3 mg/ml LP1-LP3 were significantly higher than those of the other pools and the control cultures without serum, except 3.3 mg/ml LP2, which resulted statistically in a similar number of cells than that with 3.3 mg/ml LP1-LP3. The cell number with 3.3 mg/ml LP2 was not significantly different than that with 3.3 mg/ml LP3. In addition, LP1-LP3, LP2 and LP3 had a significant increase in cell numbers between 1 and 3.3 mg/ml.

Figure 5:
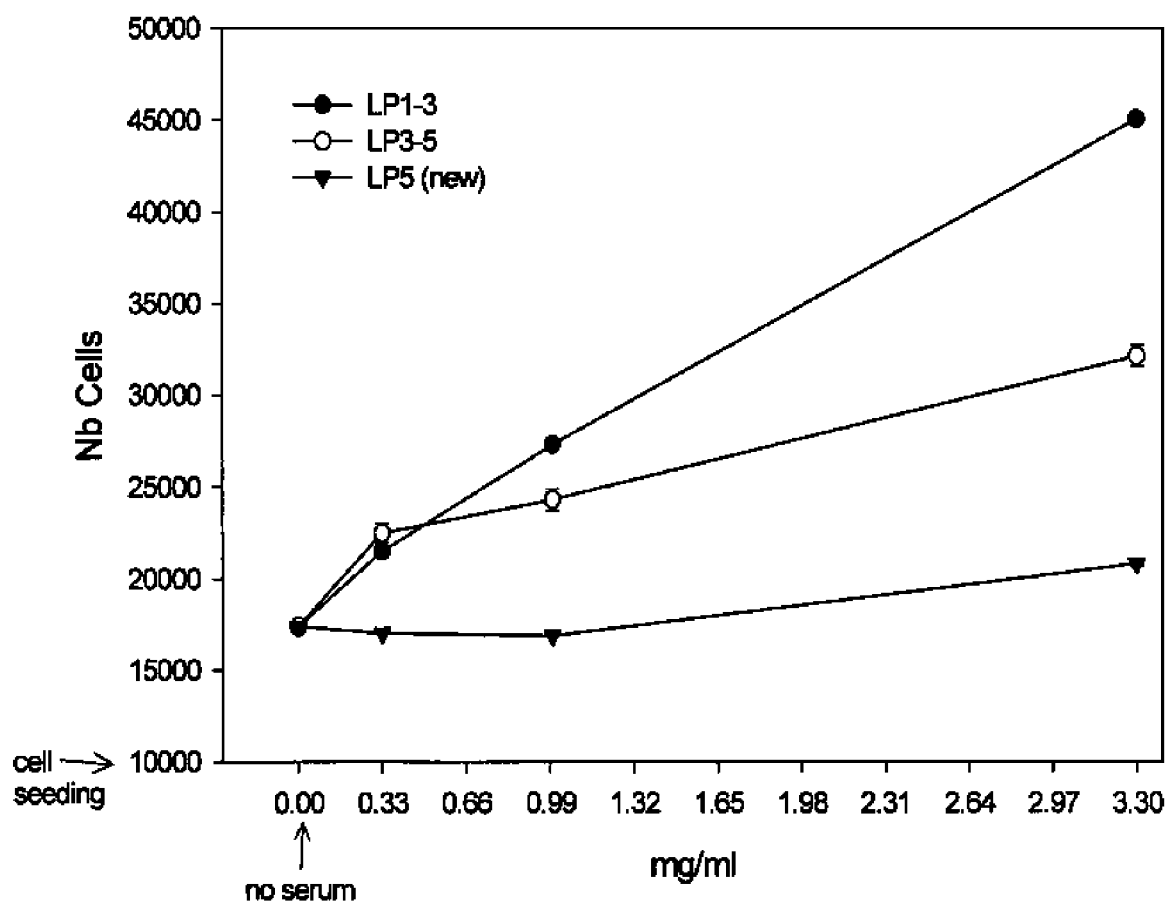
FIG. 5: Fibroblast growth (new pools, Hoechst) during 72 hr exposure.

A third set of experiments was conducted with new pools LP1-LP3, LP3-LP5 and LP5 (FIG. 5). The number of cells in the presence of 3.3 mg/ml LP1-LP3 was significantly higher than the other conditions. The cell number with 1.0 and 3.3 mg/ml LP3-LP5 was significantly different than 3.3 mg/ml LP5. The cell number with 1.0 mg/ml LP1-LP3 and LP3-LP5 were not found to be statistically different, but different compared to LP5 and controls.

3.3. Proliferation of HUVECs

Figure 6:
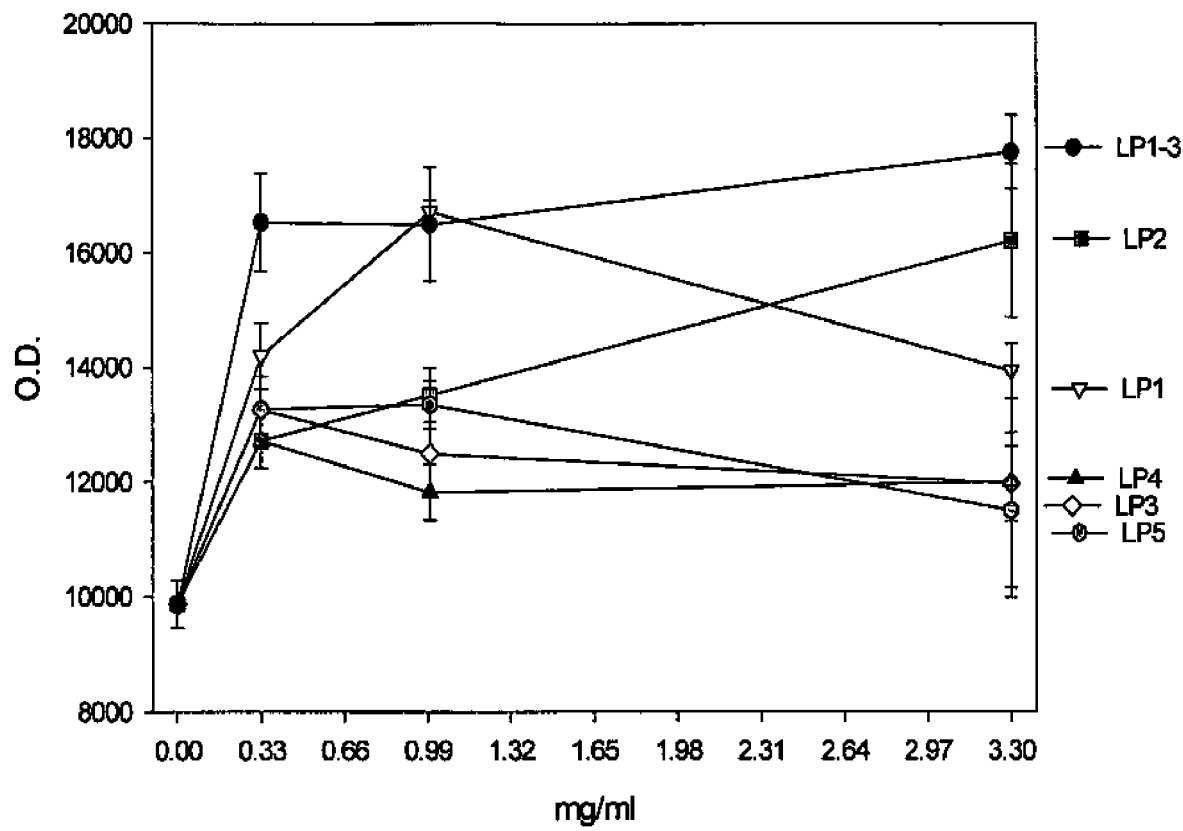
FIG. 6: Proliferation of Human Umbilical Vein Endothelial Cells (HUVECs) (Cyquant®).

The Cyquant® assay shows a significant increase in the proliferation within 12 hours in the presence of LP1-LP3 at 0.33, 1.0 and 3.3 mg/ml, as compared with the other conditions (FIG. 6). However, the values for 3.3 mg/ml LP1-LP3 were close to those with 3.3 mg/ml LP2, and those for 1.0 mg/ml LP1-LP3 were not different than those of 1.0 mg/ml LP1, LP2 and LP5.

3.4. Growth of HUVECs

A drop in cell number (from 10,000 cells at seeding time to 3,700 cells after more than 72 hrs of incubation) was observed (not shown), due to the lack of serum since these cells are very dependent on it. Once again, the exposure to LP1-LP3 significantly enhanced cell growth at the 3 doses tested, compared to the other pools and the control cultures, recovering the initial number of cells. However, the cell number with 3.3 mg/ml LP1-LP3 was close to that of 3.3 mg/ml LP3. LP3 also increased significantly the number of cells when used at 3.3 mg/ml. Conversely, a high dose of LP1 inhibited endothelial cell growth.

3.5. Collagen Synthesis and Deposition in Monolayer

Figure 7:
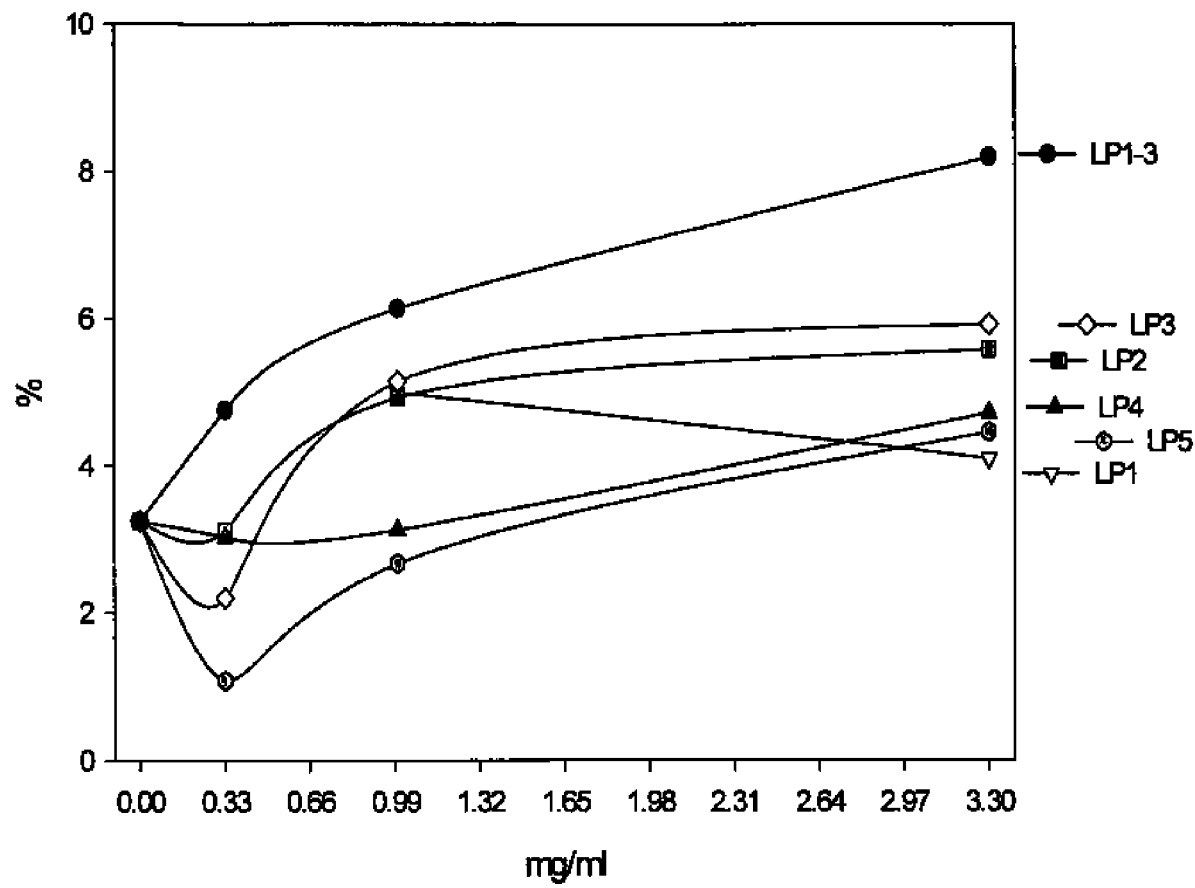
FIG. 7: Percent of proline integrated into collagen synthesis.

The presence of LP1-LP3, particularly at 1.0 and 3.3 mg/ml, enhanced collagen synthesis, as shown by increased radioactivity (FIG. 7). Similar doses of LP3 and LP2 also increased collagen synthesis, but to a lesser degree.

Phase contrast microscopy shows the extracellular matrix deposition and cells (not shown). LP2 induced matrix between cells particularly with 3.3 mg/ml. LP3 also enhanced matrix deposition at all doses tested. The behavior of cells in the presence of 1.0 and 3.3 mg/ml LP1-LP3 appeared different from the others with a reorganization of cells into a network, rarely seen in monolayer cell cultures.

In another set of experiments, the effects of LP1-LP3, LP1-LP5 and LP3-LP5 were compared. The CPM values were reported to the cell number at day 7.

Figure 8:
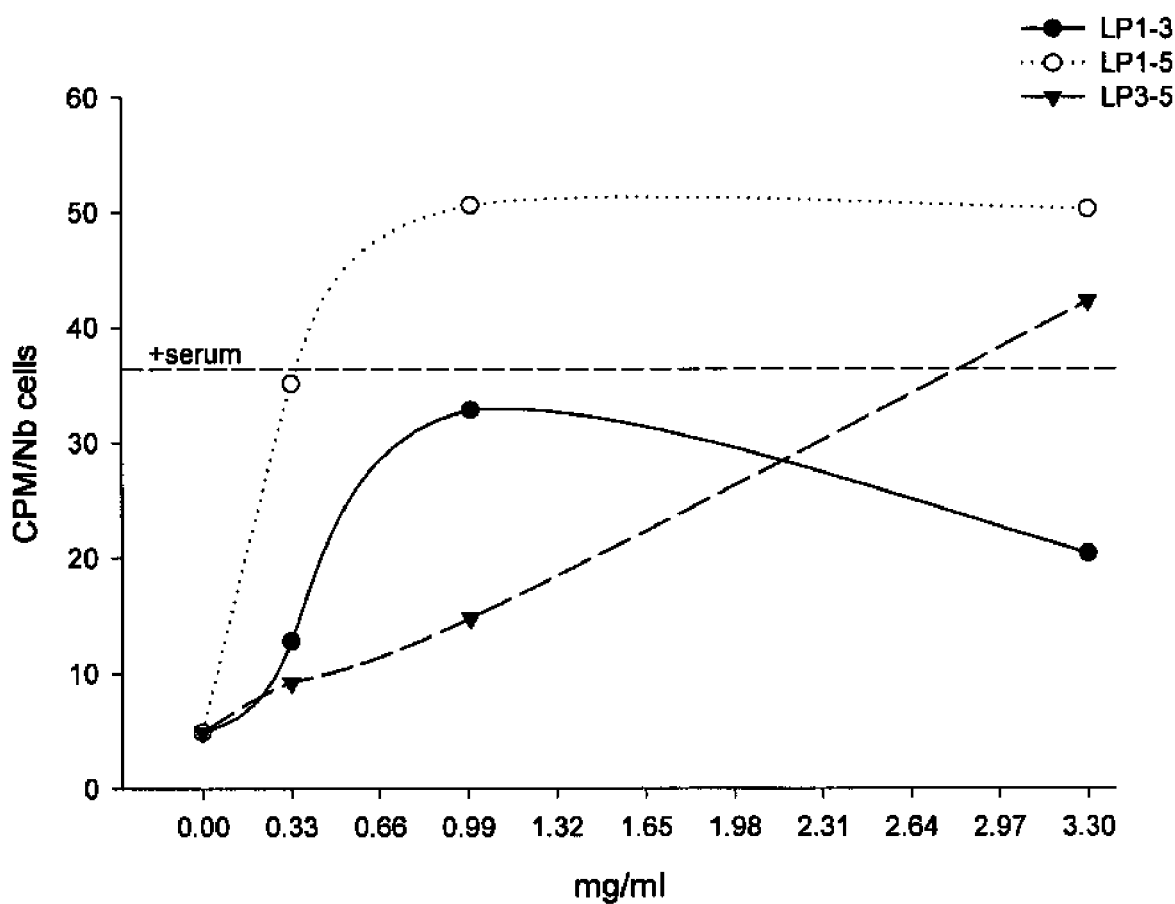
FIG. 8: Collagen Synthesis and Deposition in monolayer cell cultures as a function of cell number.

Thus, collagen synthesis and deposition per cell was particularly enhanced in the presence of 0.33, 1.0 and 3.3 mg/ml of LP1-LP5, even above the value found in the presence of serum (FIG. 8). Moreover, the values of collagen synthesis and deposition were elevated in the presence of LP1-LP3 and LP3-LP5.

3.6. 3-D Cell Cultures and Collagen Synthesis

In a first set of experiments, cell and matrix pools showed an increase in collagen synthesis and deposition with LP2 and LP3, particularly at 3.3.mg/ml (not shown). LP1-LP3 also enhanced collagen synthesis at 3.3 mg/ml, but less than LP2 and LP3. Phase contrast microscopic observation (not shown) shows numerous cells with extracellular matrix deposition at day 7, in the presence of 1 and 3 mg/ml LP2 and LP3 and 1 mg/ml LP1-LP3, all compared to the control and LP1, LP4 and LP5.

Figure 9:
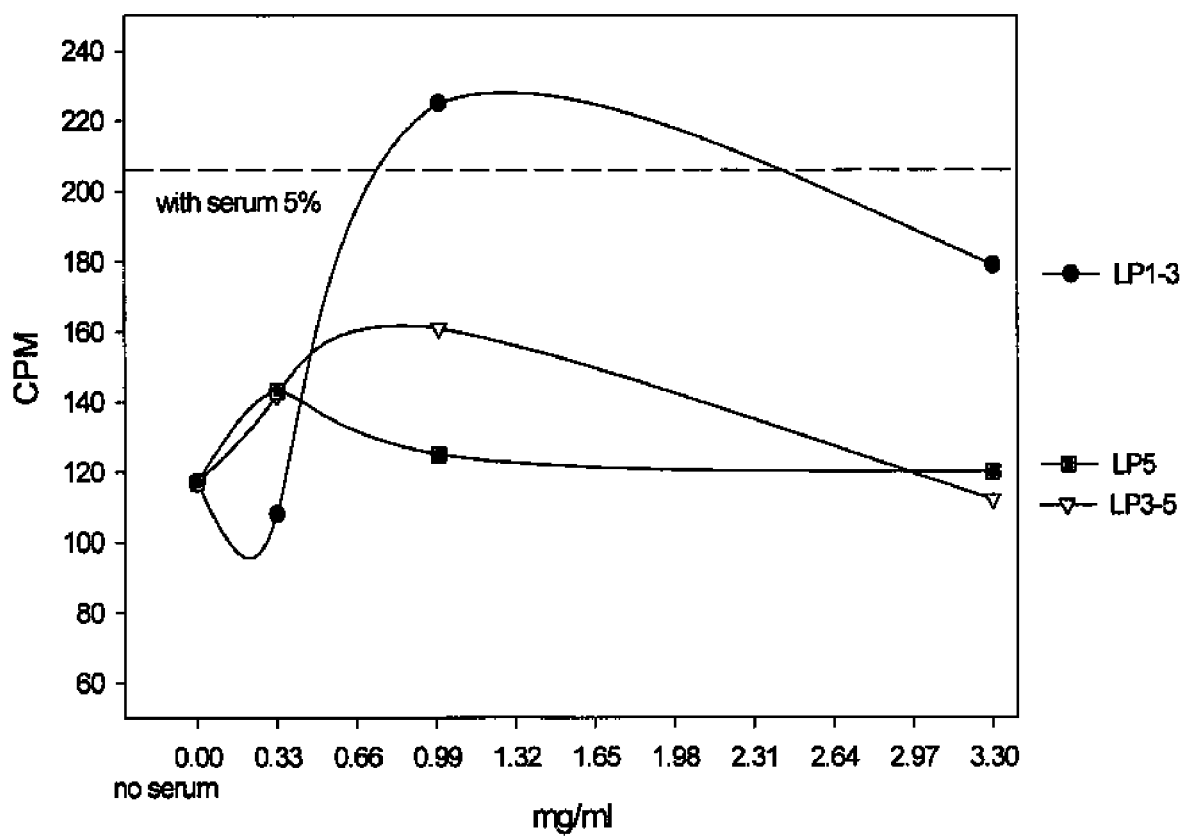
FIG. 9: Collagen synthesis and deposition by fibroblasts in fibrin gel (new LP pools).
Figure 10:
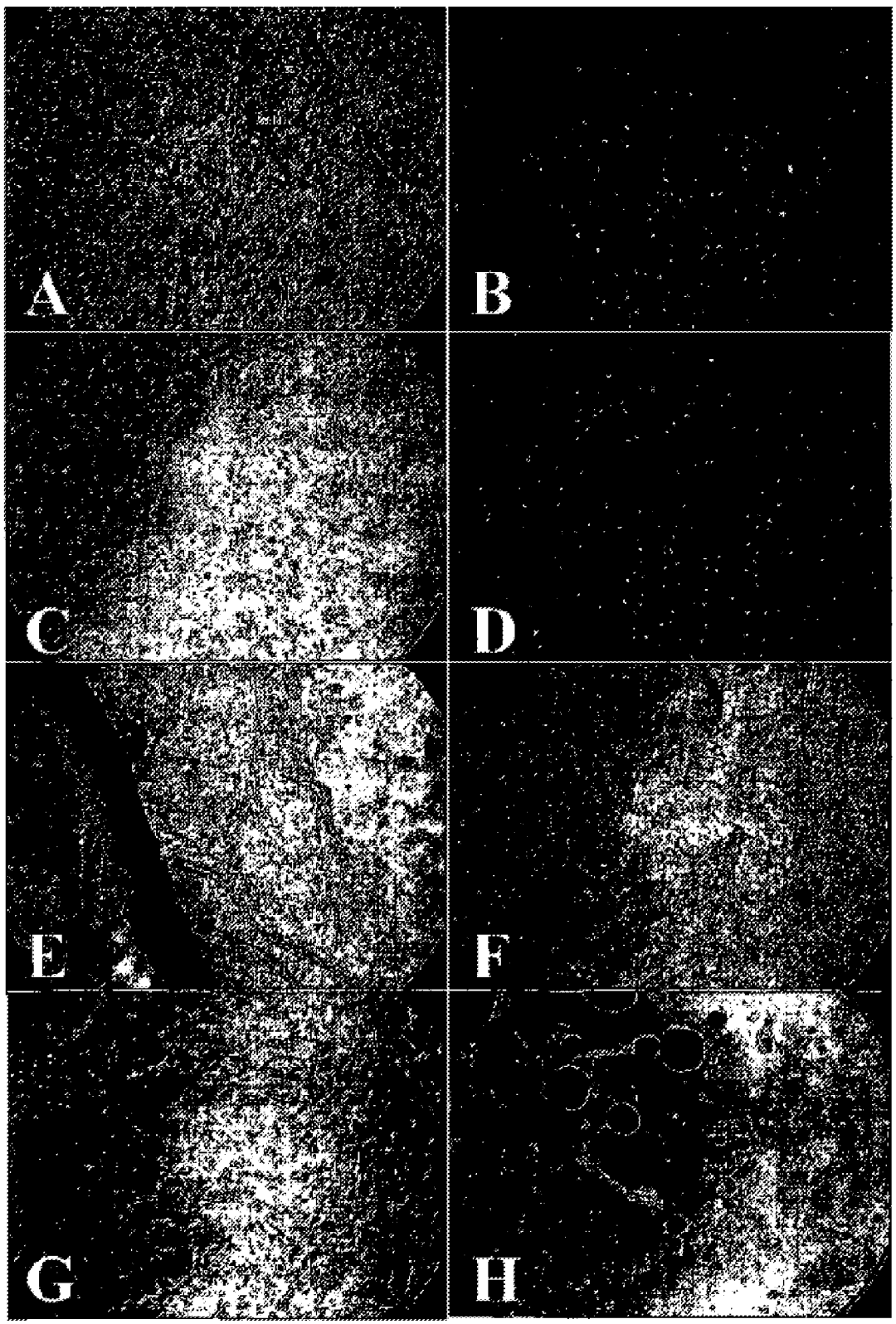
FIG. 10: Fibroblasts grown in fibrin gel for 7-9 days. In the presence of 3.3 mg/ml LP1-LP3, fibroblasts formed a dense matrix as observed on phase contrast (A) whereas the cell density was limited as observed after Hoescht staining (B). Conversely, the control culture in serum-free resulted in poor matrix density (C&D), compared to A & B. At day 8, fibroblast-containing fibrin gels were released from the culture wells and observed the next day for potential contraction as observed in the presence of 3.3 mg/ml LP1-LP3 (E) compared to control culture (F). In the presence of LP1-LP5, at 1 mg/ml, fibroblasts reorganized into a network as observed by phase contrast (G) and at 3.3 mg/ml fibrin liquefied and aggregated (H). Magnification at 20×.

A second set of experiments was performed with new LP1-LP3, LP3-LP5 and LP5 pools. Afterwards, fibrin gels were detached from the wells to allow contraction. LP1-LP3 induced an increase in collagen synthesis and deposition in the cell-matrix pools, which was close to that observed in the presence of serum (FIG. 9). LP3-LP5 induced less collagen synthesis, higher than that in the control without serum. Cell cultures were observed by phase contrast microscopy at day 8. One and 3.3 mg/ml LP1-LP3 resulted in a dense matrix with few cells, when compared particularly with the control cultures and LP5 (FIG. 10 A-D). By day 9, the contraction occurred that resulted in a floating fibrin gel. The latter was very dense in the presence of 3.3 mg/ml LP1-LP3 (FIG. 10 E-F).

Another study was performed with LP1-LP5. In the presence of LP1-LP5, fibroblasts in fibrin gels were reorganized into a network, particularly at 1 mg/ml, as shown in FIG. 10 G. Moreover, at a higher dose (3.3 mg/ml) of LP1-LP5, the fibrin gel was likely dissolved, perhaps by fribrinolysis, and some residual fibrin particles aggregated (FIG. 10 H). Measurement of collagen synthesis and deposition show less production than with LP1-LP3, with an increase at 3.3 mg/ml (not shown). However, considering the decrease in cell density by day 9, collagen production was more elevated in the presence of LP1-LP5.

4. Discussion and Conclusion

The data shows clearly that cell proliferation and growth are stimulated by the presence of LP1-LP3 (3.3-fold increase in cell number), even with doses as low as 0.33 mg/ml as observed in some experiments, and this is incrementing as a function of the dose. Similarly, but to a lesser degree, LP2, LP3, and LP3-LP5 stimulate cell growth and replication when 3.3 mg/ml is used. The stimulation of cell replication in the presence of LP1 appears only after 24 hours, and the consequence on cell number is perceptible when high dose of 10 mg/ml is used. Furthermore, the proliferation and growth of vascular endothelial cells are also stimulated by the presence of LP1-LP3. Assessment of endothelial cell growth shows an incrementing effect as a function of dose. LP3 and LP2 may also enhance cell replication and growth, but to a lesser degree.

The observation and quantification of collagen synthesis and deposition show different patterns in monolayer cell cultures versus 3-D cultures in fibrin gel, more specifically in the presence of LP2 and LP3. The two latter induce a significant increase in collagen synthesis and deposition by fibroblast in fibrin gel, particularly with 3.3 mg/ml. On the other hand, LP1-LP3 also increases, but at a less degree, collagen synthesis and deposition. LP1-LP3 also increases the organization of fibroblasts in a monolayer and more specifically in a fibrin gel (since they have a matrix to attach and migrate), as observed on micrographs. This observation is confirmed by the induction of a dense contracted matrix after days in culture. This suggests that newly formed collagen deposited in fibrin is remodeled by fibroblasts. Conversely, LP3-LP5 is less efficient to induce newly formed collagen, compared to LP1-LP3. On the other hand, LP1-LP5 induces synthetic activity as demonstrated in monolayer cultures. Whereas in 3-D fibrin gel, a differentiation activity is exhibited that involved protease activation as observed during wound remodeling.

Without wishing to be bound by any theory, the effect of LP1-LP3 on collagen synthesis and deposition may be explained by the presence of high cell density at the start of the cell cultures, due to the stimulation of cell replication as determined by the different assays. Although the LP pools are renewed at medium change during the 7-9 day period of fibroblast cultures for collagen synthesis assay, it appears that by 8 days the cell density is less than expected, and less than that observed in the control culture with serum. Thus, LP1-LP3 not only enhances fibroblast proliferation and growth, but also the biosynthetic activity of fibroblast towards the formation of collagen, its deposition, and its remodeling.

In conclusion, selective LP pools such as LP1-LP3, LP2, LP3 and LP5 have potential and specific effects on fibroblasts and endothelial cell behaviour. These pools may have a beneficial effects in wound healing and closure.

EXAMPLE 6

Proliferation and Growth of Human Fibroblasts, and Collagen Synthesis

1. Objectives of the Study

The objectives of the study were to evaluate the effect on cell behavior of the growth and differentiating factors present in three pools: LP1-LP3, LP3-LP5 and LP1-LP5. The proliferation and growth of human fibroblasts as well as their collagen synthesis were investigated in vitro for a comparative study.

2. Materials and Methods 2.1. Fibroblasts

Human fibroblasts were used in conditions similar to those described in Example 5. They were derived from the same batch used in the previous experiments.

2.2. LP Pools Concentrations

LP pools were diluted to final concentrations of 0.33, 1.0, and 3.3 mg/ml. These conditions were compared to negative control cultures in serum-free medium and positive control cultures in serum-supplemented medium.

2.3. Test of Proliferation (Cyquant® Assay); Cell Growth (Hoechst); and Collagen Synthesis in Monolayer and in Fibrin Gel Cultures ($^{14}$C-Proline)

The experimental method used was similar to that described earlier, as was the statistical comparison.

Figure 11:
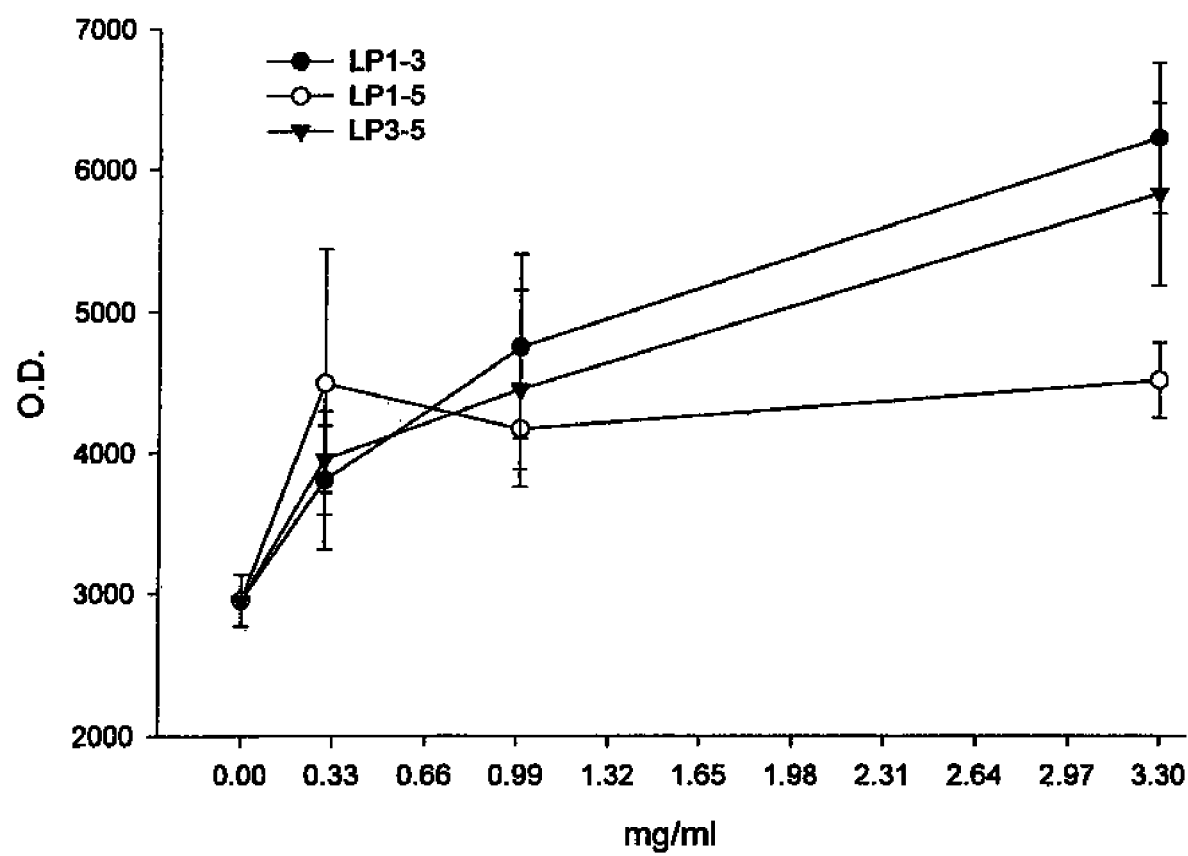
FIG. 11: Human fibroblast proliferation assay (Cyquant®); 0.33 mg/ml, 1 mg/ml and 3.30 mg/ml of growth factor pools LP1-LP3, LP1-LP5 and LP3-LP5 were tested.

3. Results 3.1. Fibroblast Proliferation (FIG. 11)

Cell proliferation after 24 hrs of culture was increased, more specifically with 1.0 and 3.3 mg/ml of LP1-LP3 and LP3-LP5 pool. Statistical analyses show that the values of 1.0 mg/ml LP1-LP3 and those of 3.3 mg/ml LP1-LP3 and LP3-LP5 were significantly higher than those of the control with no serum. Due to large variations in the values with LP1-LP5 pools, the cell proliferation values were not significantly different than those of the control.

3.2. Fibroblast Growth

Cell growth increased as a function of the doses tested for the different pools (not shown). The values of 3.3 mg/ml LP1-LP3 were significantly higher than all the other conditions, except with the control cultures in the presence of serum. The values of 3.3 mg/ml LP1-LP5 were significantly higher than all the other conditions, except LP1-LP3 and LP3-LP5 both at 3.3 mg/ml (similar), and the presence of serum (lower). The values of 3.3 mg/ml LP3-LP5 were significantly different than those of the two control cultures. Statistically, the values of 1.0 mg/ml LP1-LP3 were significantly different than those of the two control cultures. Moreover, the values at 0.33 mg/ml were different for LP1-LP3 and LP3-LP5, compared to the control cultures with no serum.

3.3. Collagen Synthesis and Deposition in Monolayer

After 7 days in cell culture, collagen synthesis and deposition was elevated for LP1-LP3 and LP3-LP5. However, when the values were reported with respect to the cell number, collagen synthesis and deposition per cell was particularly enhanced in the presence of 0.33, 1.0 and 3.3 mg/ml of LP1-LP5, even above the value found in the presence of serum. Observation of the cell cultures shows clearly less cells left in the presence of LP1-LP5, more specifically with the highest concentration tested compared to the other conditions. In the presence of serum, a dense population of cells was seen, for little quantities of formed collagen. Moreover, the values of collagen synthesis and deposition were higher in the presence of LP1-LP3 and LP3-LP5. Specifically, 3.3 mg/ml of LP3-LP5 enhanced collagen synthesis and deposition. The curve of LP1-LP3 resembles that reported earlier in monolayer cell culture. The ratio of soluble collagen versus insoluble collagen was relatively constant in any conditions tested.

3.4. 3-D Cell Cultures and Collagen Synthesis and Deposition

While experimental conditions were not optimal due to a weakness in fibrin gel formation resulting from a limited number of cells ($2\times10^5$ cells/well instead of $5\times10^5$ cells/Well), some of the data generated is of interest. In fibrin gel, LP1-LP5 behaved differently compared to LP1-LP3 and LP3-LP5. Observation of cells shows a clearly diminished number of cells as well an organisation of the fibroblasts into a network in the presence of 1.1 mg/ml LP1-LP5. This has not been observed with other components, and may correspond to dramatic cell differentiation. Moreover, LP1-LP5 at 3.3 mg/ml appeared to induce the dissolution of the fibrin gel, and it is accompanied by cell death and loss after each medium change (radioactivity value was not determined). The latter phenomenon may be induced by excessive protease activation, in particular plasminogen activators secreted by fibroblasts that have differentiated. In one instance (not shown), LP1-LP3 increased the formation of soluble and insoluble collagen slightly. However, it did not show any stimulation when the values of cpm were reported to the number of cells. LP3-LP5 increased the collagen production per cell. On the other hand, LP1-LP5 appeared to enhance collagen synthesis and deposition when the values were reported to the number of cells.

4. Discussion and Conclusion

The three LP pools of pools stimulate cell proliferation and cell growth, particularly the LP1-LP3 at high dose of 3.3 mg/ml. Although the stimulation of cell growth by LP1-LP3 occurs, collagen synthesis and deposition was limited when compared specifically with LP1-LP5. The latter induces a significant increase of collagen formation in monolayer cell culture and in 3D fibrin gel. Moreover, the presence of LP1-LP5 results in a cell differentiation into cord-like structures, but at high doses proteases are likely to be involved.

In conclusion, the LP1-LP5 pool of factors induces cell differentiation along with synthetic activity rather than proliferative and growth activity. The synthetic activity is accurately demonstrated in monolayer cultures, while the differentiation activity is exhibited in 3D fibrin gels.

EXAMPLE 7

Cell Proliferation Effect of LP1-LP5 Pool of Growth Factors on Chondrocytes

Figure 12:
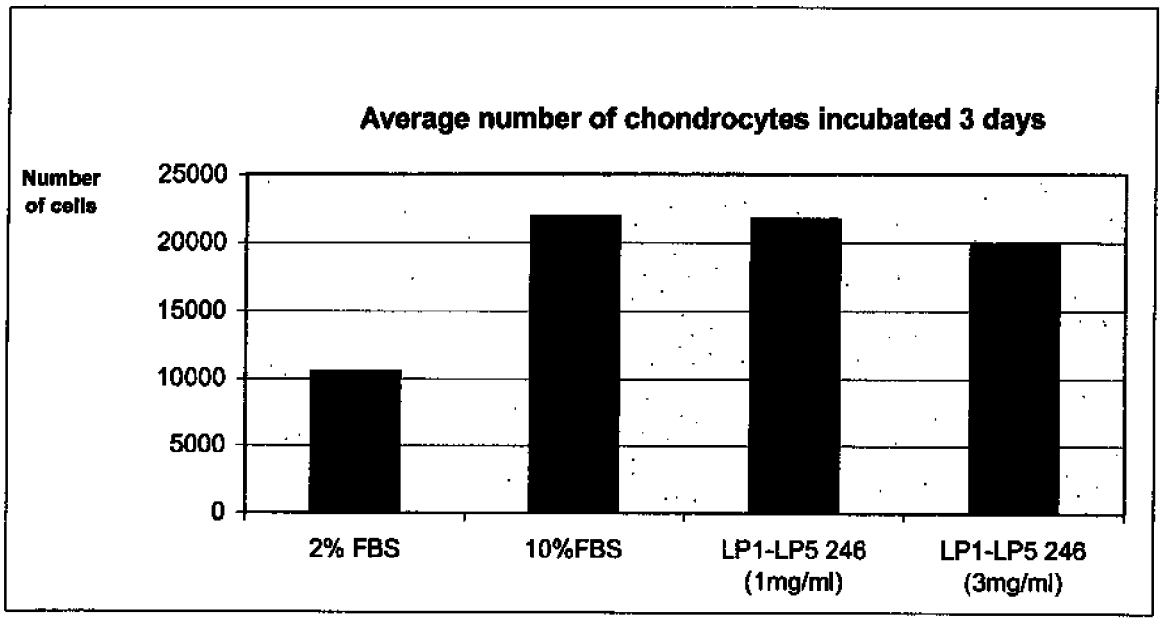
FIG. 12: Effect on chondrocyte proliferation of 1 mg/ml and 3 mg/ml LP1-LP5 incubated 3 days.
Figure 13:
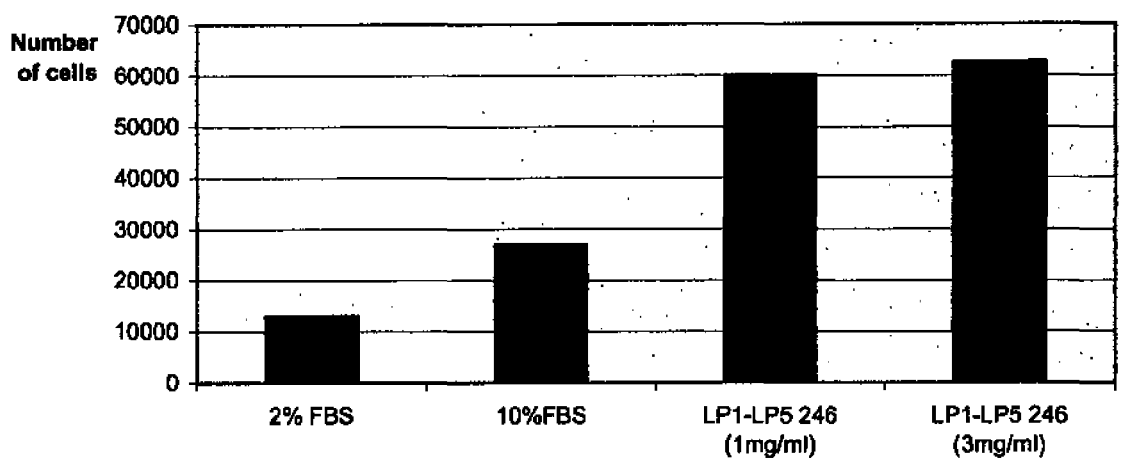
FIG. 13: Effect on chondrocyte proliferation of 1 mg/ml and 3 mg/ml LP1-LP5 incubated 7 days.
Figure 14:
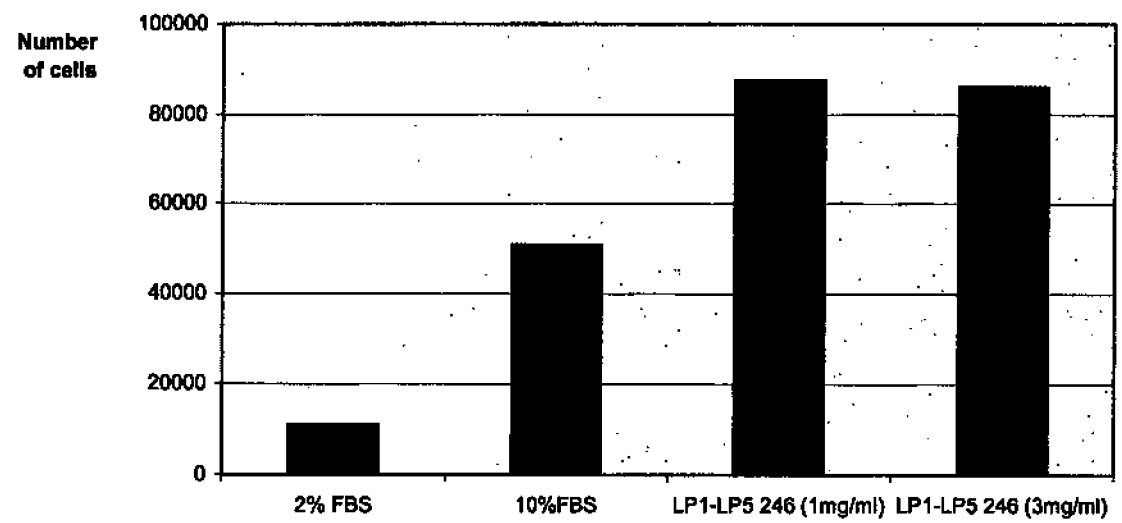
FIG. 14: Effect on chondrocyte proliferation of 1 mg/ml and 3 mg/ml LP1-LP5 incubated 10 days.
Figure 15:
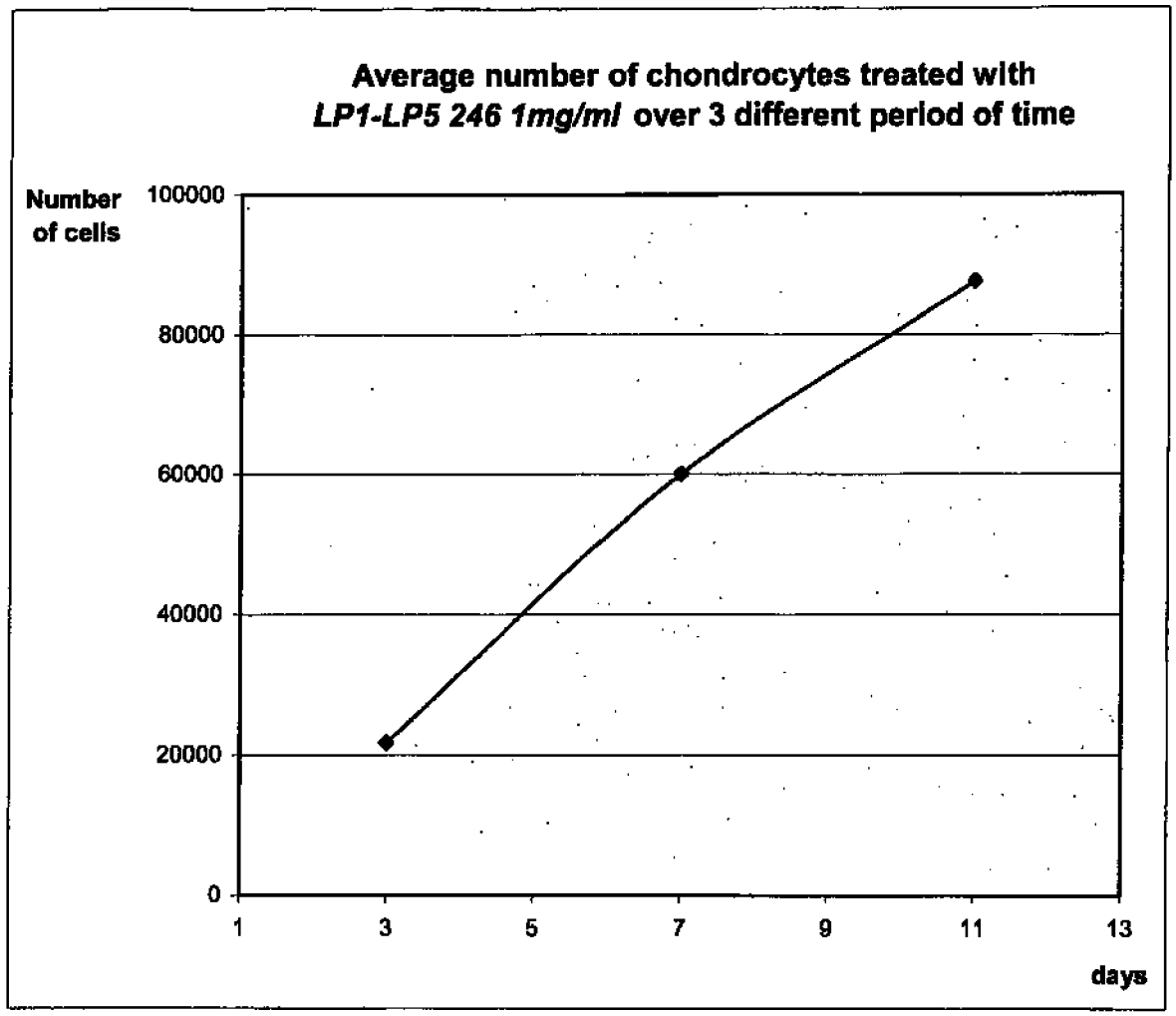
FIG. 15: Average number of chondrocytes treated with LP1-LP5 over three different periods of time.

The effect on chondrocyte proliferation of the LP1-LP5 pool of growth factors was measured. FIGS. 12, 13 and 14 show the effect on chondrocyte proliferation of 1 mg/ml and 3 mg/ml LP1-LP5 after 3 days, 7 days and 10 days, respectively. Two and ten percent fetal bovine serum (FBS) served as controls. FIG. 15 shows the proliferation (number of chondrocytes) due to 1 mg/ml of LP1-LP5 over the same three periods of time.

As may be appreciated from the results, chondrocyte proliferation was enhanced in the presence of both 1 mg/ml and 3 mg/ml LP1-LP5. FIGS. 12, 13 and 14 reveal that after three days the proliferation is similar to that for cells incubated with FBS. However, by days 7 and 10, chondrocyte proliferation is markedly increased in the presence of LP1-LP5.

EXAMPLE 8

Wound Healing Capabilities of LP1-LP3, LP1-LP5 and LP3-LP5 Pools of Growth Factors The wound healing capabilities of LP1-LP3, LP1-LP5 and LP3-LP5 were investigated in a guinea pig model. Briefly, 9 male guinea pigs were used in the experiments. (The protocol was accepted by the Committee for the Protection of Animals of the Centre hospitalier universitaire de Québec (CHUQ).) Under general anesthesia (isoflurane with oxygen) and using dermatological punches, four 6-mm (diameter) punch biopsies were made in the backs of each animal.

The wounds were arranged so that three wounds were positioned on one side of each animal's back in order to receive a sample of one of the three pools to be tested (2 mg per wound of LP1-LP3, LP1-LP5 or LP3-LP5), and one wound was positioned on the other side of the back to receive physiological liquid (0.9% saline solution). This arrangement was devised to minimize cross-contamination between the wounds. The animals were sacrificed after 7, 14 and 28 days according to the following schedule: one animal given an LP1-LP3 dosage was sacrificed after 7 days, a second after 14 days and a third after 28 days; one animal given an LP1-LP5 dosage was sacrificed after 7 days, a second after 14 days and a third after 28 days; and one animal given an LP3-LP5 dosage was sacrificed after 7 days, a second after 14 days and a third after 28 days.

Figure 16:
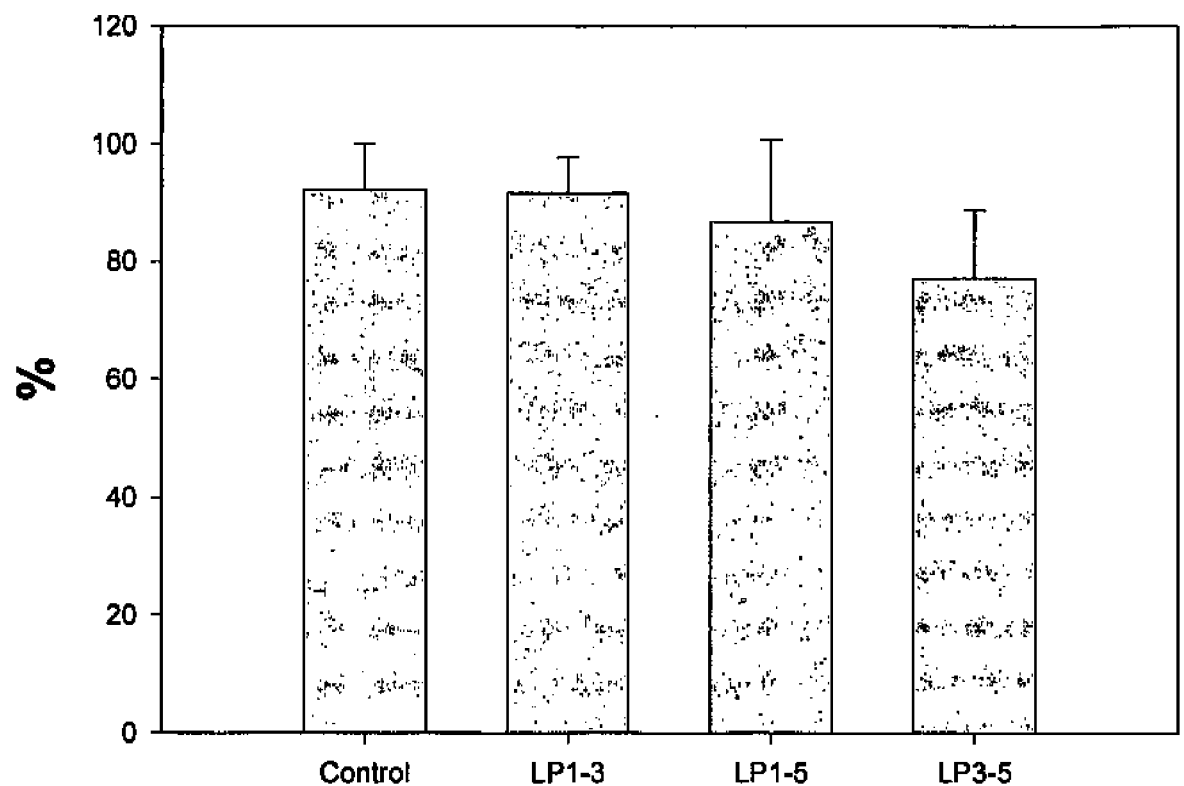
FIG. 16: Epidermal covering (epidermization) at day 7 due to LP1-LP3, LP1-LP5 and LP3-LP5.
Figure 17:
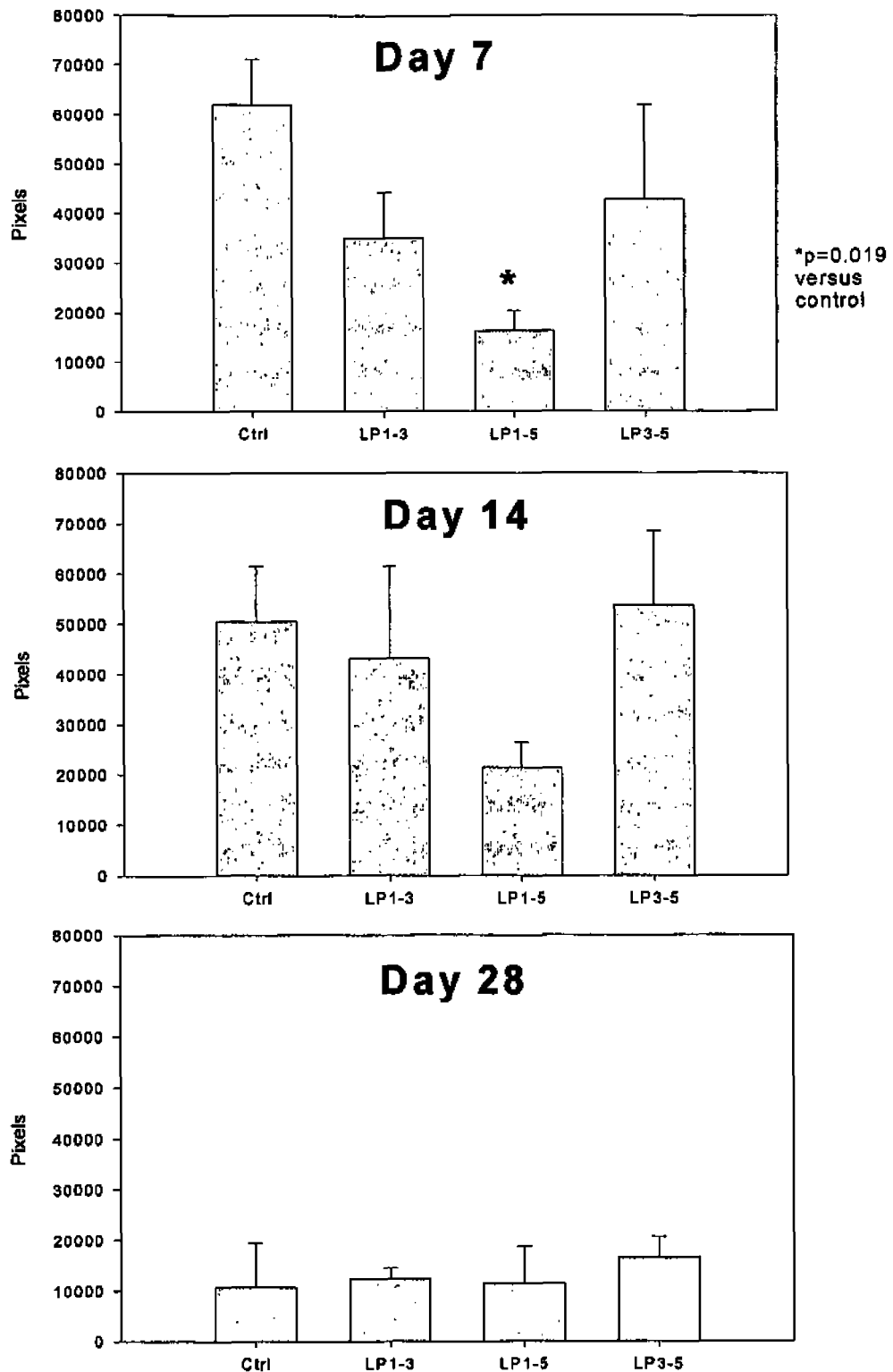
FIG. 17: Diminution of wound areas (granulation tissue) caused by LP1-LP3, LP1-LP5 and LP3-LP5 after 7 days, 14 days and 28 days.
Figure 19:
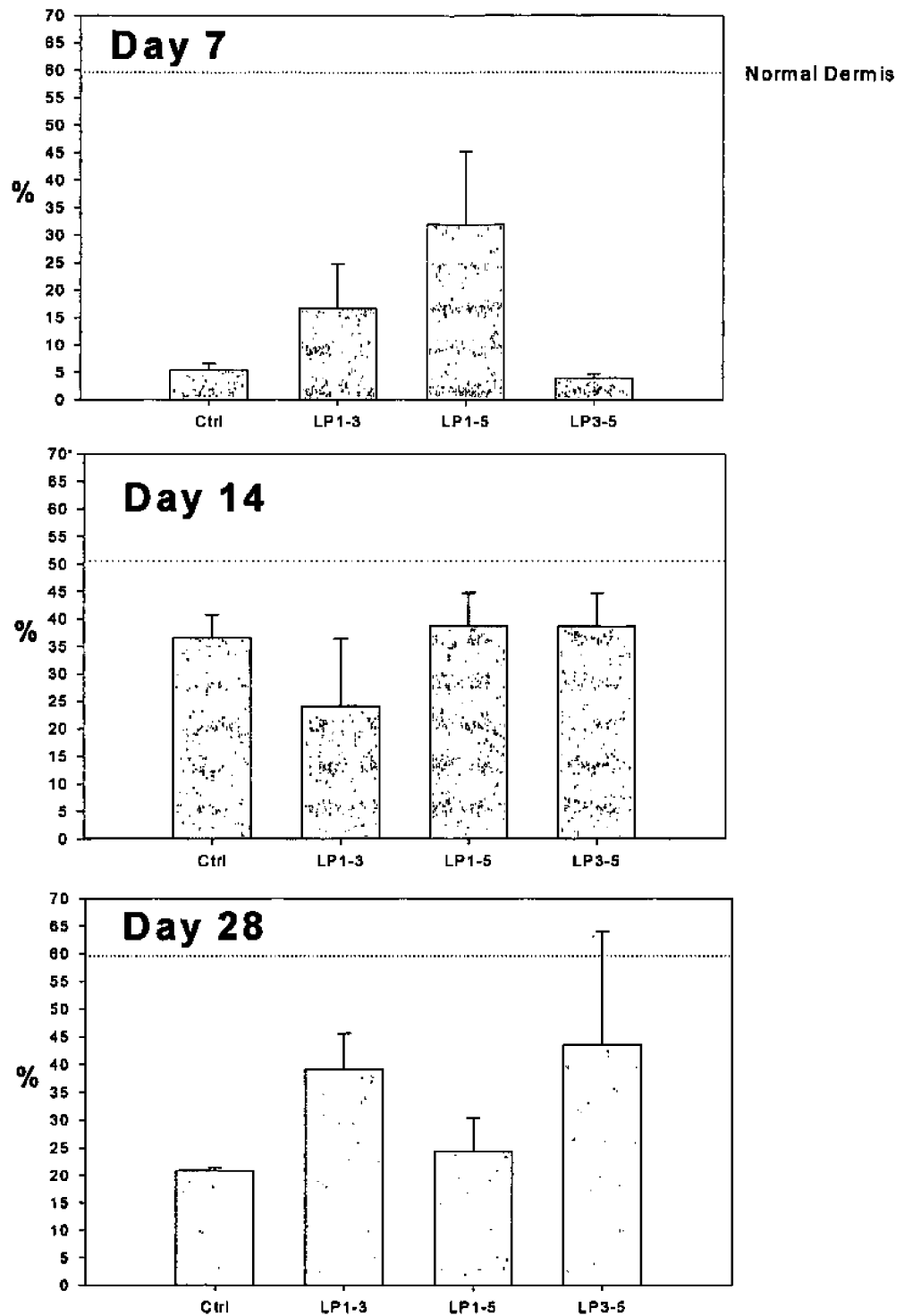
FIG. 19: Formation of collagen fibers due to LP1-LP3, LP1-LP5 and LP3-LP5 after 7 days, 14 days and 28 days.

FIG. 16 shows the epidermal covering (epidermization) at day 7 of the three pools. FIG. 17 reveals the diminution of wound areas (granulation tissue) after 7 days, 14 days and 28 days. FIG. 18 shows the wound or dermal thickness after 7 days and 14 days, while FIG. 19 reveals the degree of newly-formed collagen fibers after 7 days, 14 days and 28 days.

Figure 20:
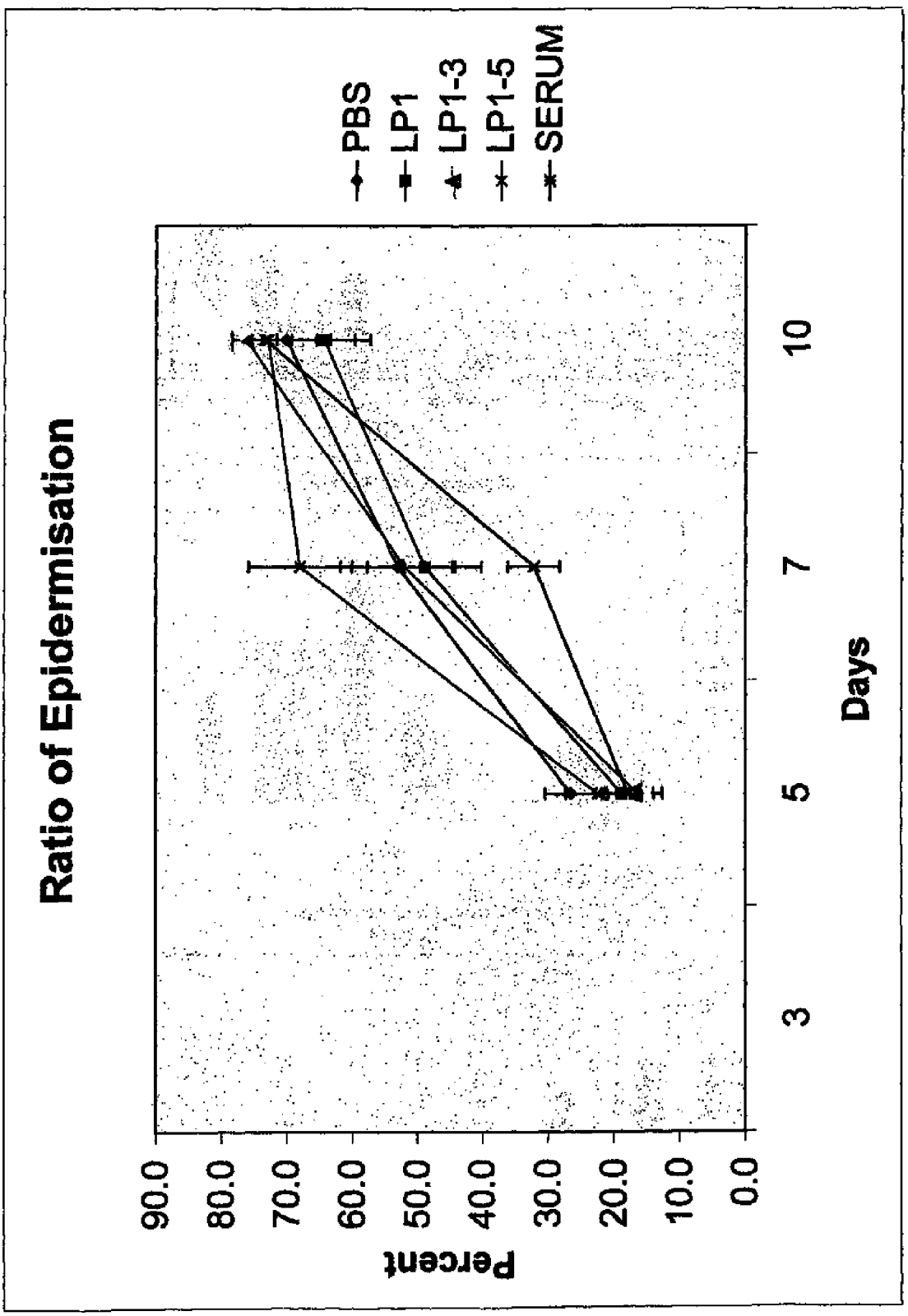
FIG. 20: Ratio of epidermization for fractions LP1 and LP1-LP3, and LP1-LP5, after 5, 7 and 10 days.

In a separate but related experiment, the ratio of epidermization resulting from pools LP1, LP1-LP3 and LP1-LP5 after 5, 7 and 10 days was investigated (see FIG. 20). The results reveal that wound closure occurs much more rapidly in the presence of these pools than they would otherwise (see percent epidermization of pools compared to serum at 7 days, for example). Interestingly, the wound closures were devoid of keloids.

Quantification has allowed the demonstration of the reduction in surface area occupied by granulation tissue, as well as a diminution in its thickness, especially early on (at days 7 and 14) with the LP1-LP5 pool of growth factors. This reduction is accompanied by a rapid deposition of collagen (particularly at day 7), which does not occur to a significantly greater degree subsequently. It should also be noted that at day 7, in the presence of LP1-LP5, wound contraction is much augmented in comparison to the other conditions at this time. These observations would suggest that LP1-LP5 has a moderate scarring activity, while avoiding excess tissue repair as is observed during foetal scarring, for example. No differences in the migration and epidermal covering have been found, which leads to the supposition that LP1-LP5 acts preferentially on granulation tissue, under the assay conditions used (in vivo).

EXAMPLE 9

Precocious Maturation (Differentiation) of Brush Cells

Figure 21:
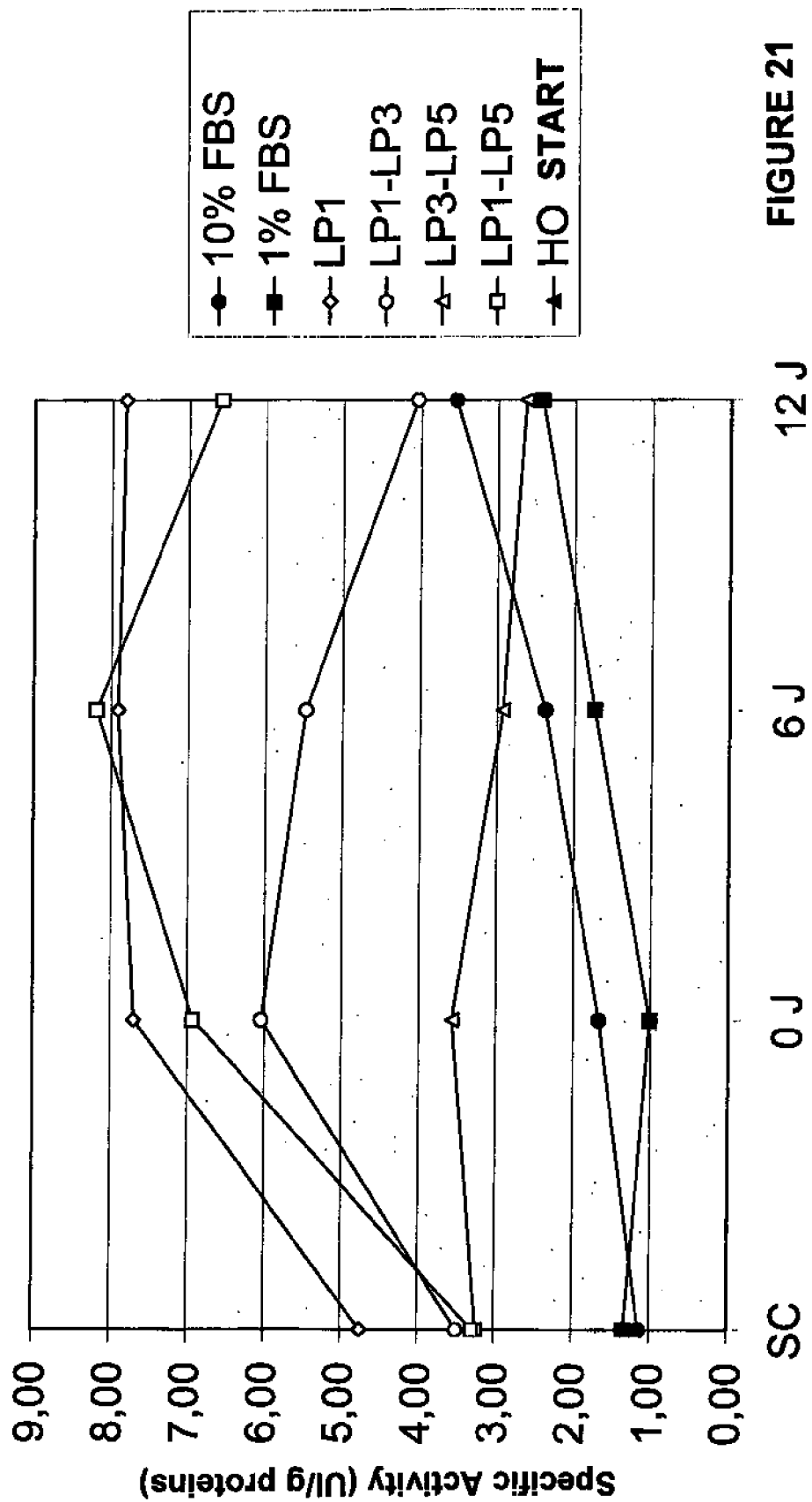
FIG. 21: Specific activity of alkaline phosphatase at days 0, 6 and 12 for brush cells exposed to LP1, LP1-LP3, LP1-LP5 and LP3-LP5.
Figure 22:
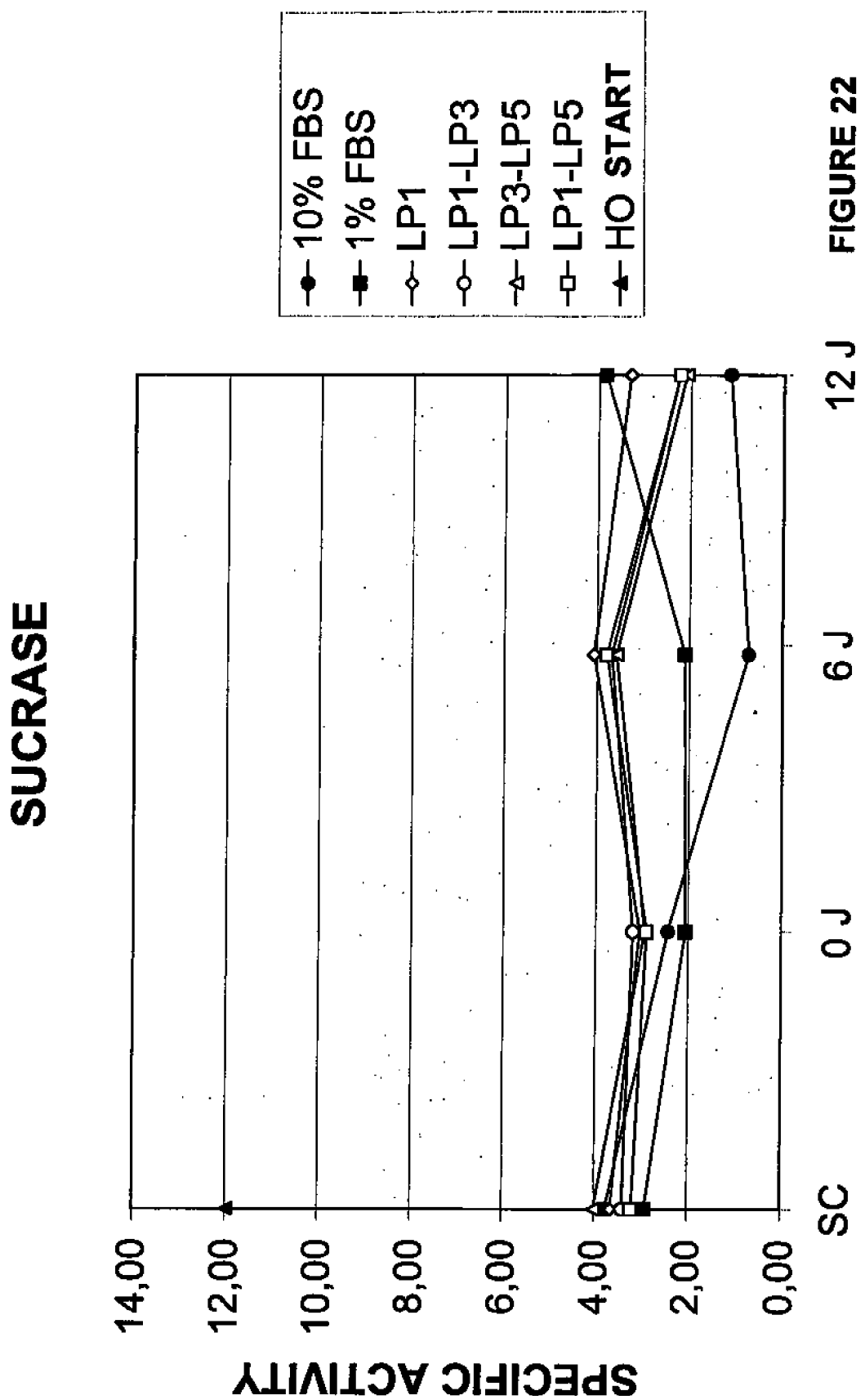
FIG. 22: Specific activity of sucrase at days 0, 6 and 12 for brush cells exposed to LP1, LP1-LP3, LP1-LP5 and LP3-LP5.
Figure 23:
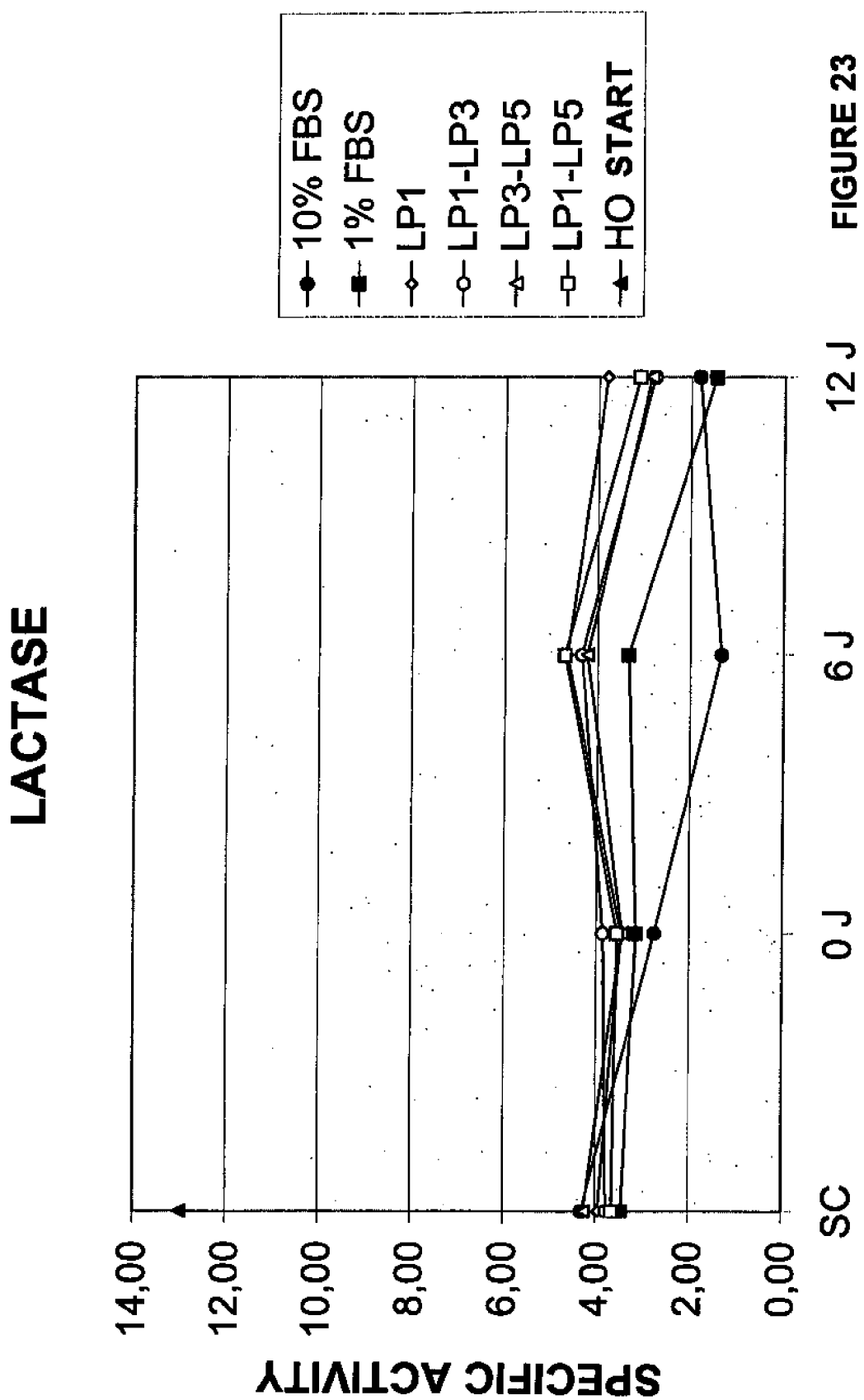
FIG. 23: Specific activity of lactase at days 0, 6 and 12 for brush cells exposed to LP1, LP1-LP3, LP1-LP5 and LP3-LP5.

Brush cells incubated with 1% serum along with growth factor pools LP1-LP3, LP1-LP5 and LP3-LP5 differentiate faster than cells incubated solely with 1% or 10% serum. As may be seen from FIG. 21, the specific activity of alkaline phosphatase is significantly increased for cells exposed to LP1 and LP1-LP5, even before confluence. An increase in the specific activities of sucrase and lactase is also observed, post confluence, especially with pools LP1 and LP1-LP5, as may be observed from FIGS. 22 and 23, respectively.

Interestingly, brush cells, pre-confluence, incubated with the different pools, and particularly with LP1 and LP1-LP5, demonstrated a degree of polarization that is significant when compared to cells incubated in 1% and 10% serum (not shown). These cells exhibited a cuboidal morphology and appeared to be squeezed more tightly against each other.

The above observations have significant implications as far as the digestive epithelium is concerned. The use of the growth factor pools speeds up the maturation and differentiation of brush cells, leading them to generate their digestive enzymes (lipases, amylases and proteases) more rapidly. The pools could therefore be used to treat compromised digestive systems, such as those of premature and mature newborns or individuals suffering from GI tract ailments (inflammations and obstructions).

EXAMPLE 10

Uses or Applications for Various Growth Factors

The growth factors that are isolated through the novel process of the present invention may be used in a number of applications, including: cosmetics, cosmeceuticals, nutraceuticals and food additives, as well as in dermatological, pharmaceutical, medical and veterinary applications. Suggested applications for the specific growth factors found in individual fractions (see FIG. 1(B) and FIG. 3 for the factors found in the various fractions) are listed in Table 5.

Interestingly, fraction LP5, which is the filtrate passing through the microfilter of 5 kDa (FIG. 1(B)), may also be useful in a number of applications. LP5 has been found to contain a wealth of vitamins, trace elements, amino acids, natural peptides and salts, among other pools. It can therefore be used as a diluent in the manufacture of cosmetic products and as an effluent in the preparation of nutraceutical substances, among other applications.

TABLE 5

Uses or Applications for Growth Factors in Specific Fractions

| Fraction | Applications |
|---|---|
| PPT (cheese) | Emergency nutrient for prized calfs born by Caesarean section (IGMs and primary casein), trace IgG and IgM |
| W541 - 0.2 µm | Emergency nutrient pH 4.50 = soluble casein and partially hydrolyzed globulins For prized calfs born by Caesarean section not having access to maternal colostrum |
| LP1 | Nutraceutical (digestive inflammation) |
| LP2 | Nutraceutical (digestive inflammation) (with traces of primary casein) |
| LP3 | Cosmetic and cosmeceutical; Nutraceutical (digestive inflammation of the bowel) (without casein and gamma-globulin) |
| LP4 | Dermal pool of mature growth factors of low molecular weight for transdermal applications (for the manufacture of high end cosmetics without bacteria or viruses) |
| LP5* | Food and beverage supplement; vitamins, salts, amino acids, lactose, oligoelements and small peptides |
| LP1-LP3 | Cell proliferation and some differentiation (collagen secretion and maturation) |
| LP3-LP5 | Cell proliferation but even more differentiation (collagen secretion and maturation) relative to LP1-LP3 |
| LP1-LP5 | Cell proliferation and differentiation (collagen secretion and maturation); contractility of the dermis; elaboration of specific digestive enzymes, etc. |

*NB: The LP5 extract includes the following: Lactose (13%); calcium (1.2%); sodium (0.3%); phosphorus (0.6%); magnesium (0.2%); potassium (0.8%); alanine (2.9 g/100 g protein); arginine (1.5 g/100 g protein); aspartic acid + asparagine (9.5 g/100 g protein); cystein (1.9 g/100 g protein); glutamic acid + glutamine (20.1 g/100 g protein); glycine (2 g/100 g protein); histidine (1 g/100 g protein); isoleucine (4.4 g/100 g protein); leucine (10 g/100 g protein); lysine (4.5 g/100 g protein); methionine (2.2 g/100 g protein); phenylalanine (6.1 g/100 g protein); proline (3.6 g/100 g protein); serine (7.2 g/100 g protein); threonine (7.3 g/100 g protein); tryptophan (0.9 g/100 g protein); tyrosine (7.9 g/100 g protein); valine (6.9 g/100 g protein); IGF1 (monomer 7 kDa and dimer 14 kDa) (0.1-0.7 mg/100 g); TGF-β2 (85% and TGF-β) (0.06-0.46 g/100 g); lactoferrin (0.16 g/100 g); lactoperoxydase (9.1 mg/100 g); lysozyme (16 mg/100 g); vitamin A (5 µg/g MG); vitamin B12 (23 µg/100 g); choline (0.3 mg/100 g); folic acid (3.8 µg/100 g); riboflavin (23 µg/100 g); thiamin (0.28 mg/100 g); biotin (13 µg/100 g); nicotinic acid (0.46 mg/100 g); ascorbic acid (12 µg/100 g); and pantothenic acid (0.8 mg/100 g).

Although the present invention has been described hereinabove by way of preferred embodiments thereof, it can be modified without departing from the spirit, scope and nature of the subject invention, as defined in the appended claims.

The invention claimed is:

1. A process for isolating growth and differentiating factors from colostrum, comprising:
   (a) subjecting a colostral solution to partial hydrolysis by adjusting the pH to about 3.75-3.85;
   (b) vortexing the partially hydrolyzed colostral solution obtained in step (a) for about 30 to 90 minutes;
   (c) adjusting the pH of the vortexed colostral solution obtained in step (b) to about 4.52-4.55;
   (d) centrifuging the pH-adjusted colostral solution obtained in step (c), and setting aside the resulting supernatant;
   (e) running the supernatant through a filtration system comprising one or more filtration columns; and
   (f) obtaining a fraction containing pools of growth and differentiating factors therefrom, all the while ensuring that the temperature during the process never exceeds about 38° C.

2. The process as defined in claim 1, further comprising lyophilizing said pools of growth and differentiating factors.

3. A The process as defined in claim 1, wherein said filtration system comprises one or more filtration columns selected from the following filtration sizes: 0.2 µm, 300 kDa, 150 kDa, 50 kDa and 15 kDa.

4. The process as defined in claim 1, wherein said filtration system is comprised of one of the following: a 0.2 µm column; a 300 kDa column; a 150 kDa column; a 50 kDa column; a 15 kDa column; a 0.2 µm column linked with a 150 kDa column; a 0.2 µm column linked with a 15 kDa column; and a 150 kDa column linked with a 15 kDa column.

* * * * *